US012365916B2

(12) United States Patent
Schaser et al.

(10) Patent No.: US 12,365,916 B2
(45) Date of Patent: Jul. 22, 2025

(54) ADAPTER-BASED RETROVIRAL VECTOR SYSTEM FOR THE SELECTIVE TRANSDUCTION OF TARGET CELLS

(71) Applicant: Miltenyi Biotec B.V. & Co. KG, Bergisch Gladbach (DE)

(72) Inventors: Thomas Schaser, Rosrath (DE); Nicole Cordes, Cologne (DE); Joerg Mittelstaet, Cologne (DE); Andrew Kaiser, Rosrath (DE)

(73) Assignee: MILTENYI BIOTEC B.V. & CO. KG, Bergisch Gladbach (DE)

( * ) Notice: Subject to any disclaimer, the term of this patent is extended or adjusted under 35 U.S.C. 154(b) by 763 days.

(21) Appl. No.: 16/760,869

(22) PCT Filed: Oct. 26, 2018

(86) PCT No.: PCT/EP2018/079486
§ 371 (c)(1),
(2) Date: Apr. 30, 2020

(87) PCT Pub. No.: WO2019/086351
PCT Pub. Date: May 9, 2019

(65) Prior Publication Data

US 2021/0180083 A1 Jun. 17, 2021

(30) Foreign Application Priority Data

Oct. 30, 2017 (EP) .................................... 17199170

(51) Int. Cl.
*C12N 15/86* (2006.01)
*C07K 14/005* (2006.01)
*C07K 14/705* (2006.01)

(52) U.S. Cl.
CPC ............ *C12N 15/86* (2013.01); *C07K 14/005* (2013.01); *C07K 14/70503* (2013.01);
(Continued)

(58) Field of Classification Search
CPC ................ C07K 2319/33; C12N 15/86; C12N 2740/10045; C12N 2740/16045; C12N 2760/18022; C12N 2760/18422
See application file for complete search history.

(56) References Cited

U.S. PATENT DOCUMENTS 9,486,539 B2 11/2016 Lee
2016/0333374 A1 11/2016 Anastaso et al.

FOREIGN PATENT DOCUMENTS

EP 2844746 3/2015
WO 2008037458 A2 4/2008
(Continued)

OTHER PUBLICATIONS

Navaratnarajah, C. K., et al., Jan. 2020, Receptor-mediated cell entry of paramyxoviruses: Mechanisms, and consequences for tropism and pathogenesis, J. Biol. Chem. 295(9):2771-2786.*
(Continued)

*Primary Examiner* — Jeffrey S Parkin
(74) *Attorney, Agent, or Firm* — Kilpatrick Townsend & Stockton LLP

(57) ABSTRACT

The present invention provides a composition comprising i) a pseudotyped retroviral vector particle or virus-like particle thereof comprising a) one envelope protein with antigen-binding activity, wherein said envelope protein is a recombinant protein that does not interact with at least one of its native receptor(s) and is fused at its ectodomain to a polypeptide comprising an antigen binding domain specific for a tag of a tagged polypeptide, and wherein said envelope protein is protein G, HN or H derived from the Paramyxoviridae family, and b) one envelope protein with fusion activity derived from the Paramyxoviridae family, and ii) said tagged polypeptide, wherein said tagged polypeptide binds specifically to an antigen expressed on the surface of a target cell, thereby transducing the target cell with said
(Continued)

retroviral vector particle or thereby inducing uptake of the virus-like particle into the target cell. A pharmaceutical composition thereof and an in vitro method for transduction of targets cells with said vector particle are also disclosed.

26 Claims, 15 Drawing Sheets

Specification includes a Sequence Listing.

(52) U.S. Cl.
CPC ...... *C07K 2319/02* (2013.01); *C07K 2319/03* (2013.01); *C07K 2319/33* (2013.01); *C12N 2740/10045* (2013.01); *C12N 2740/16045* (2013.01)

(56) References Cited

FOREIGN PATENT DOCUMENTS

| | | | |
|---|---|---|---|
| WO | 2013104728 | A1 | 7/2013 |
| WO | 2013148327 | A1 | 10/2013 |

OTHER PUBLICATIONS

Rima, B., et al., 2019, ICTV virus taxonomy profile: Paramyxoviridae, J. Gen. Virol. 100:1593-1594.*
Azarm K. D., and B. Lee, Jan. 2020, Differential features of fusion activation within the Paramyxoviridae, Viruses 12(161):1-28.*
Anliker et al., "Specific Gene Transfer to Neurons, Endothelial Cells and Hematopoietic Progenitors with Lentiviral Vectors", Nature Methods vol. 7, No. 11, Nov. 2020, pp. 929-935.
Bender et al., "Receptor-Targeted Nipah Virus Glycoproteins Improve Cell-Type Selective Gene Delivery and Reveal a Preference for Membrane-Proximal Cell Attachment", PLoS Pathogens, Jun. 9, 2016, 28 pages.
Buchholz, C., Cattaneo, R., Cichutek, K., and Funke, S. (2009). Pseudotypisierung retroviraler vektoren, verfahren zur herstellung und verwendung davon für gezielten gentransfer und screening mit hohem durchsatz, EP2066795 B9.
Chen et al., "Fusion Protein Linkers: Property, Design and Functionality", Advanced Drug Delivery Reviews 65 (10), Oct. 15, 2013, 32 pages.
Ucker et al., Targeted Transduction of T Cell Subsets for Immunotherapy of Cancer and Infectious Disease (Humboldt-Universität zu Berlin, Lebenswissenschaftliche Fakultät), Sep. 9, 2016, 104 pages.
Enkirch et al., "Targeted Lentiviral Vectors Pseudotyped with the Tupaia Paramyxovirus Glycoproteins", Gene Therapy 20, 30 pages.
Frecha et al., "Stable Transduction of Quiescent T Cells Without Induction of Cycle Progression by a Novel Lentiviral Vector Pseudotyped with Measles Virus Glycoproteins", Blood 112, 2008, pp. 4843-4852.
Hoop, "Modulation of the Transduction of Pseudotyped Lentiviral Vectors and Their Application for the Production of Recombinant Proteins", A Master Thesis Submitted to the Faculty of ETH Zurich in the Department of Bioengineering, ETH Library, Feb. 28, 2014, 101 pages.
Kaikkonen et al., "(Strept)avidin-displaying lentiviruses as versatile tools for targeting and dual imaging of gene delivery", Gene Therapy 16, 2009, pp. 894-904.
Khetawat et al., "A Functional Henipavirus Envelope Glycoprotein Pseudotyped Lentivirus Assay System", Virology Journal 7, 312, 14 pages.
Liu et al., "Ablation of Nectin4 Binding Compromises CD46 Usage by a Hybrid Vesicular Stomatitis Virus/measles Virus", Journal of Virology vol. 88, No. 4, pp. 2195-2204.
Masse et al., "Measles Virus (MV) Hemagglutinin: Evidence that Attachment Sites for MV Receptors SLAM and CD46 Overlap on the Globular Head", Journal of Virology vol. 78, No. 17, Sep. 2004, pp. 9051-9063.
Masse et al. "Identification of a Second Major Site for CD46 Binding in the Hemagglutinin Protein from a Laboratory Strain of Measles Virus (MV): Potential Consequences for Wild-Type MV Infection". Journal of Virology vol. 76, No. 24, Dec. 2002, pp. 13034-13038.
Metzner et al., "Postexit Surface Engineering of Retroviral/Lentiviral Vectors", BioMed Research International, vol. 2013, 9 pages.
Morizono et al., "A Versatile Targeting System with Lentiviral Vectors Bearing the Biotin-Adaptor Peptide", The Journal of Gene Medicine, vol. 11, Aug. 2009, pp. 655-663.
Nakamura et al., "Rescue and Propagation of Fully Retargeted Oncolytic Measles Viruses", Nature Biotechnology, vol. 23, Feb. 2005, pp. 209-214.
Nakamura et al., "Antibody-Targeted Cell Fusion", Nature Biotechnology, vol. 22, No. 3, Mar. 2004, pp. 331-336.
Palomares et al., "Nipah Virus Envelope-Pseudotyped Lentiviruses Efficiently Target EphrinB2-Positive Stem Cell Populations in Vitro and Bypass the Liver Sink When Administered in Vivo", Joumal of Virology, vol. 87, Feb. 2013, pp. 2094-2108.
Patterson et al., "Structural and Functional Studies of the Measles Virus Hemagglutinin: Identification of a Novel Site Required for CD46 Interaction", Virology 256, 1999, pp. 142-151.
Rasbach et al., "The Receptor Attachment Function of Measles Virus Hemagglutinin Can Be Replaced with an Autonomous Protein That Binds Her2/neu While Maintaining Its Fusion-Helper Function", Journal of Virology vol. 87, Nov. 11, Jun. 2013, pp. 6246-6256.
Roux et al., "A Versatile and Potentially General Approach to the Targeting of Specific Cell Types by Retroviruses: Application to the Infection of Human Cells by Means of Major Histocompatibility Complex Class I and Class II Antigens by Mouse Ecotropic Murine Leukemia Virus-Derived Viruses", Proceedings of the National Academy of Sciences of the United States of America, vol. 86, Dec. 1989, pp. 9079-9083.
Snitkovsky et al., "Targeting Retroviral Vector Infection to Cells that Express Heregulin Receptors Using a TVA-Heregulin Bridge Protein", Virology 292, 2002, pp. 150-155.
Tahara et al., "Measles Virus Infects both Polarized Epithelial and Immune Cells by Using Distinctive Receptor-Binding Sites on Its Hemagglutinin", Journal of Virology, vol. 82, No. 9, May 2008, pp. 4630-4637.
Uhlig et al., "Lentiviral Protein Transfer Vectors Are an Efficient Vaccine Platform and Induce a Strong Antigen-Specific Cytotoxic T Cell Response", Journal of Virology, vol. 89, 2015, pp. 9044-9060.
Vongpunsawad et al., "Selectively Receptor-Blind Measles Viruses: Identification of Residues Necessary for SLAM- or CD46-Induced Fusion and Their Localization on a New Hemagglutinin Structural Model", Journal of Virology, vol. 78, Jan. 2004, pp. 302-313.
Cordes N et al: 11 P229 Adapter mediated transduction with lentiviral vectors: A novel tool for cell-type specific gene transfer, Journal for Immunotherapy of Cancer, vol. 6, No. Suppl. 1, Nov. 6, 2018 (Nov. 6, 2018), p. 116.

* cited by examiner

FIG 1A-C

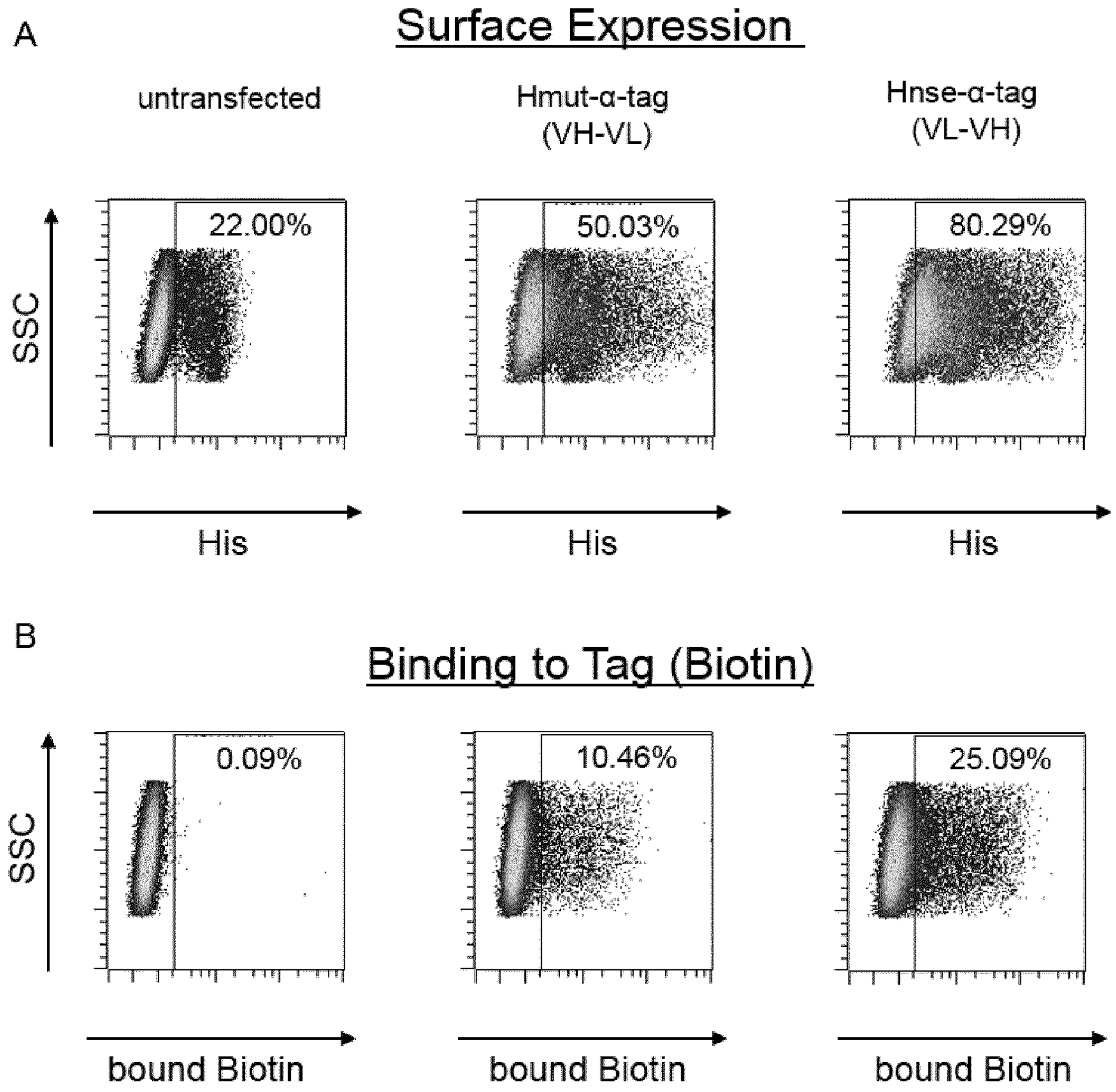
FIG 3A-B

A
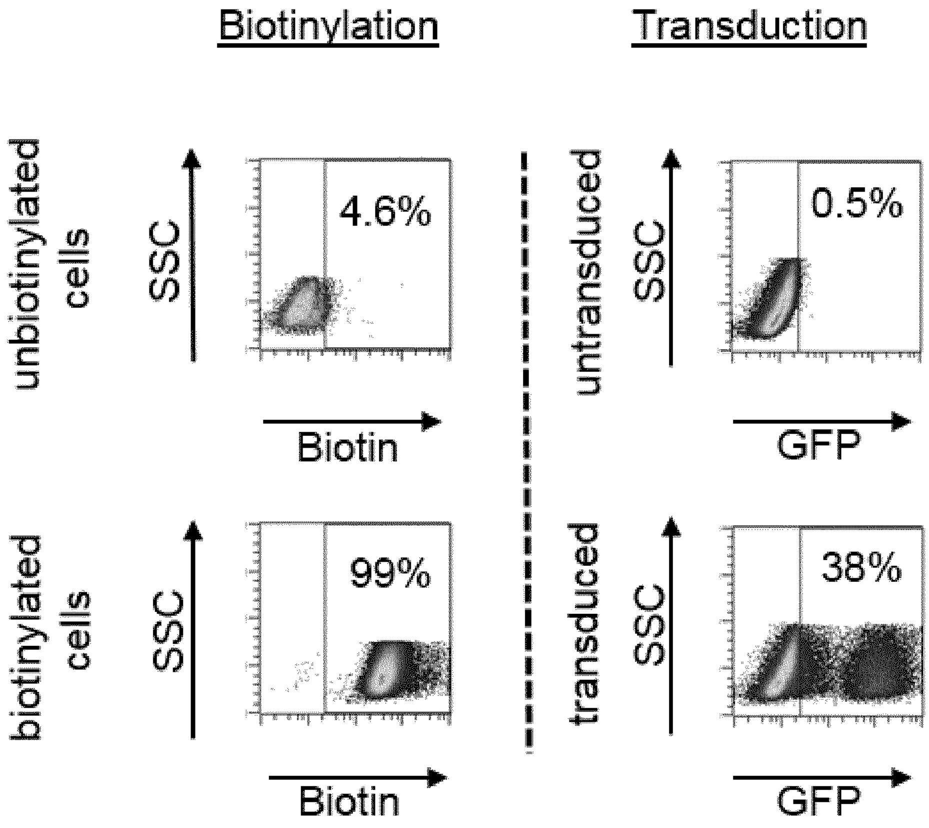
B
| Vector | Titer |
|---|---|
| α-CD46-LV | $1.5x10^6$ TU/ml |
| α-CD20-LV | $1.71x10^6$ TU/ml |
| α-tag-LV (VH-VL) | $9.5x10^4$ TU/ml |
| α-tag-LV (VL-VH) | $2.1x10^5$ TU/ml |
FIG 4A-B

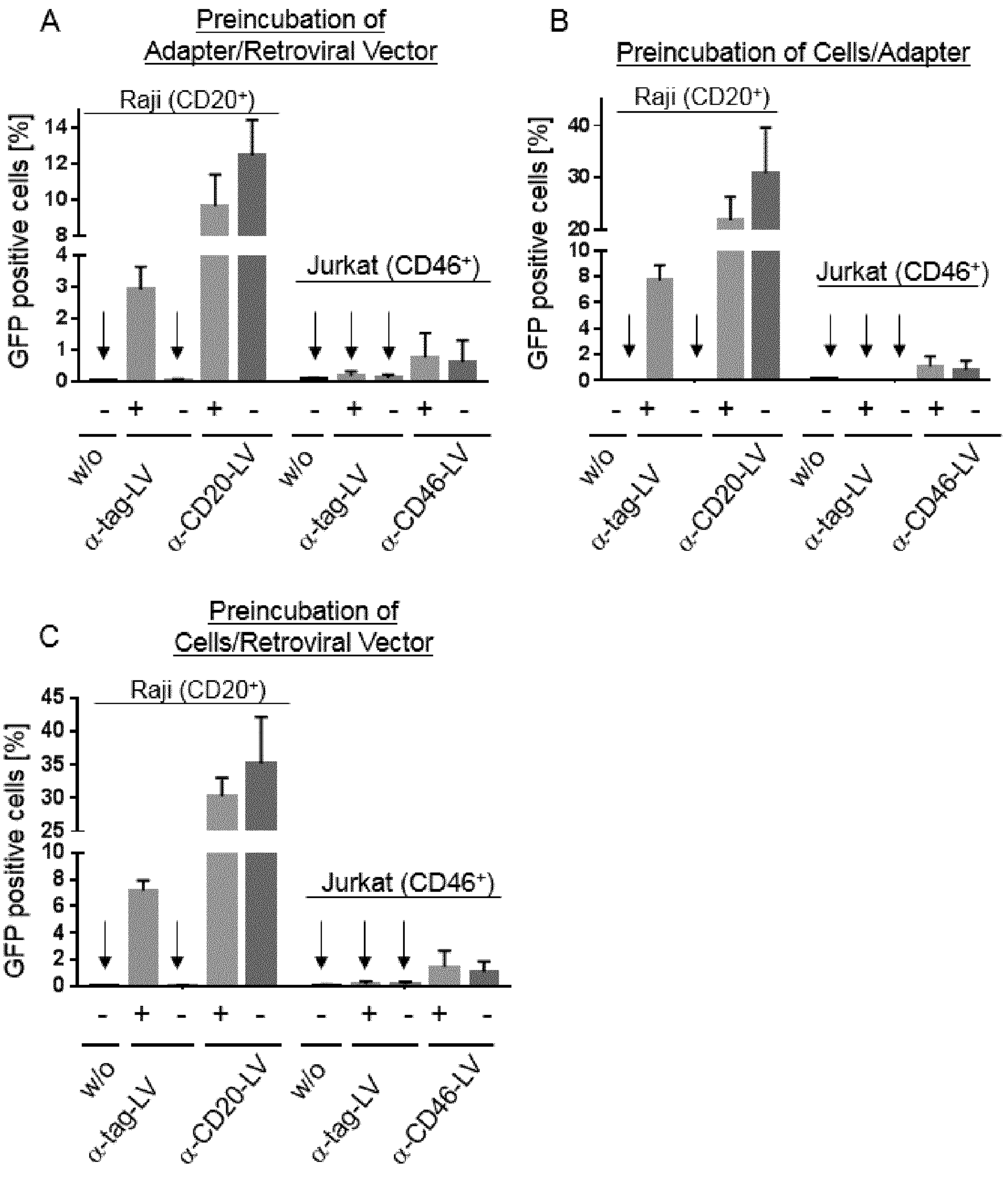
FIG 5A-C

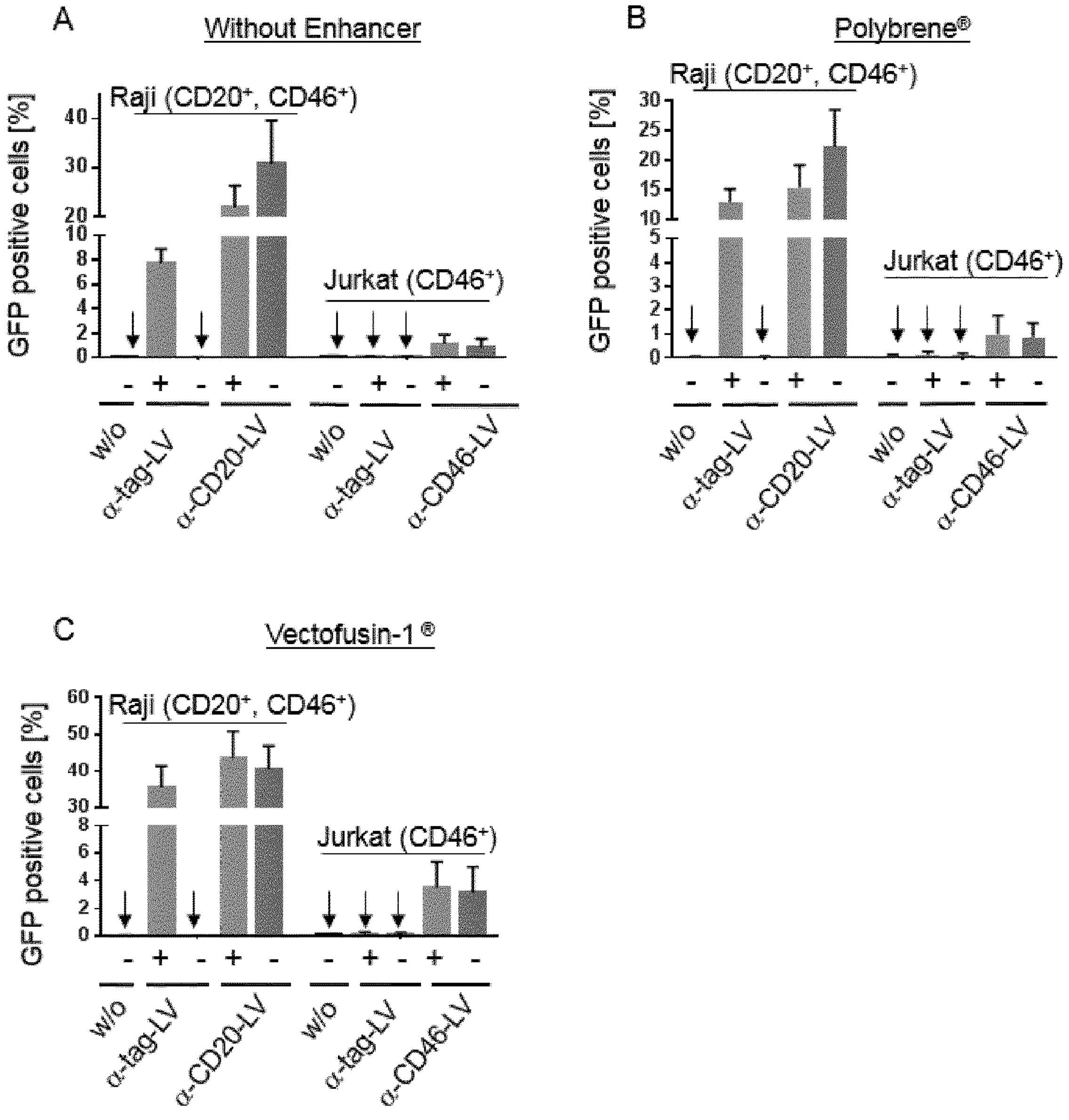
FIG 6A-C

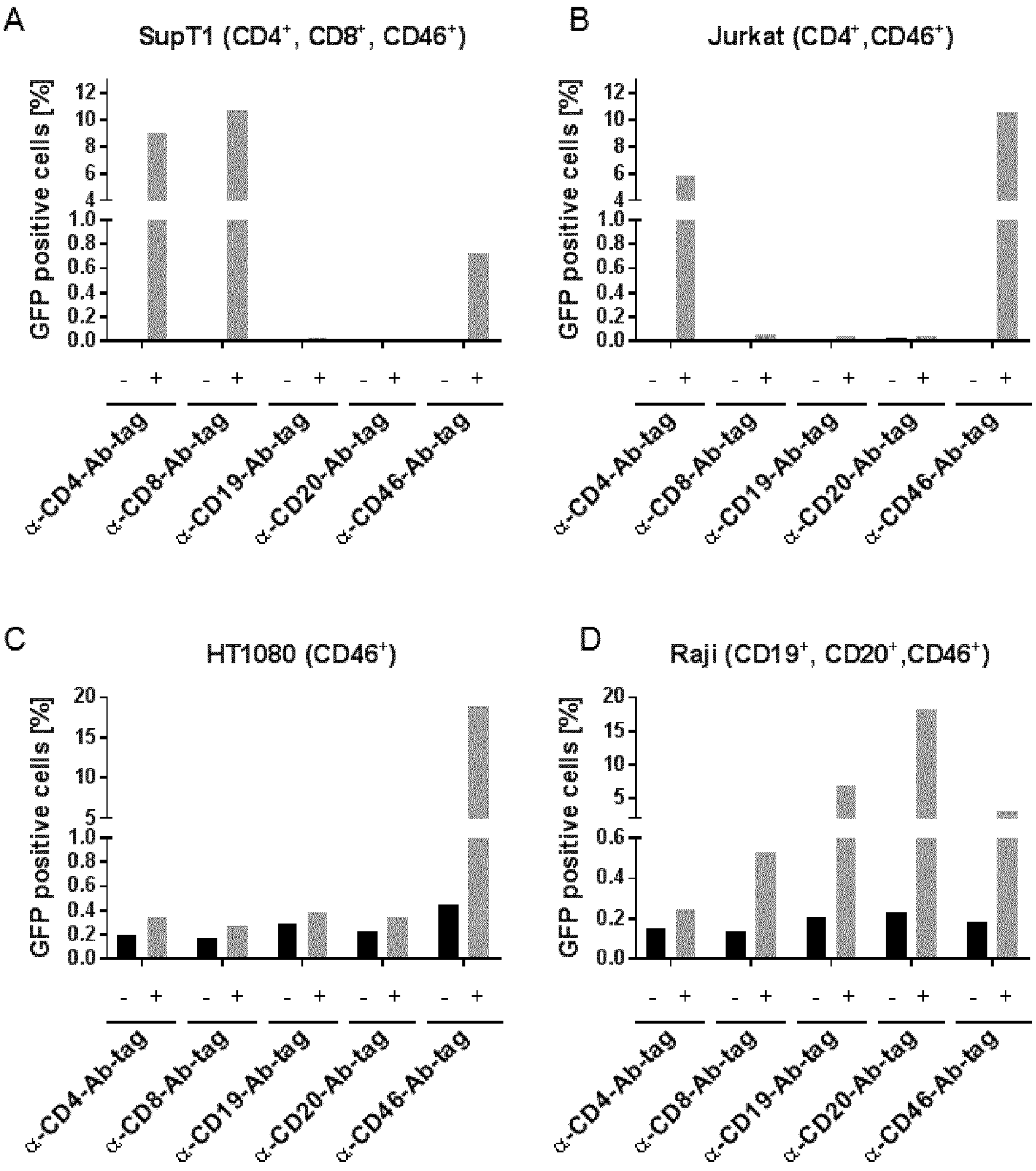
FIG 7A-D

| | | Off-target (left quadrants) | | On-target (right quadrants) | |
|---|---|---|---|---|---|
| | | GFP- | GFP+ | GFP- | GFP+ |
| untransduced | α-CD4-Ab-tag | 99.71% | 0.29% | 99.63% | 0.37% |
| | α-CD8-Ab-tag | 99.78% | 0.22% | 99.83% | 0.17% |
| | α-CD20-Ab-tag | 100.00% | 0.00% | 99.81% | 0.19% |
| | α-CD46-Ab-tag | 100.00% | 0.00% | 99.70% | 0.30% |
| Transduced without adapter | α-CD4-Ab-tag | 99.77% | 0.23% | 99.50% | 0.50% |
| | α-CD8-Ab-tag | 99.71% | 0.29% | 99.97% | 0.03% |
| | α-CD20-Ab-tag | 100.00% | 0.00% | 99.83% | 0.17% |
| | α-CD46-Ab-tag | 100.00% | 0.00% | 99.71% | 0.29% |
| Transduced with adapter | α-CD4-Ab-tag | 99.15% | 0.85% | 50.40% | 49.60% |
| | α-CD8-Ab-tag | 99.18% | 0.82% | 63.49% | 36.51% |
| | α-CD20-Ab-tag | 99.89% | 0.11% | 52.23% | 47.77% |
| | α-CD46-Ab-tag | 91.30% | 8.70% | 88.85% | 11.15% |

FIG 8B

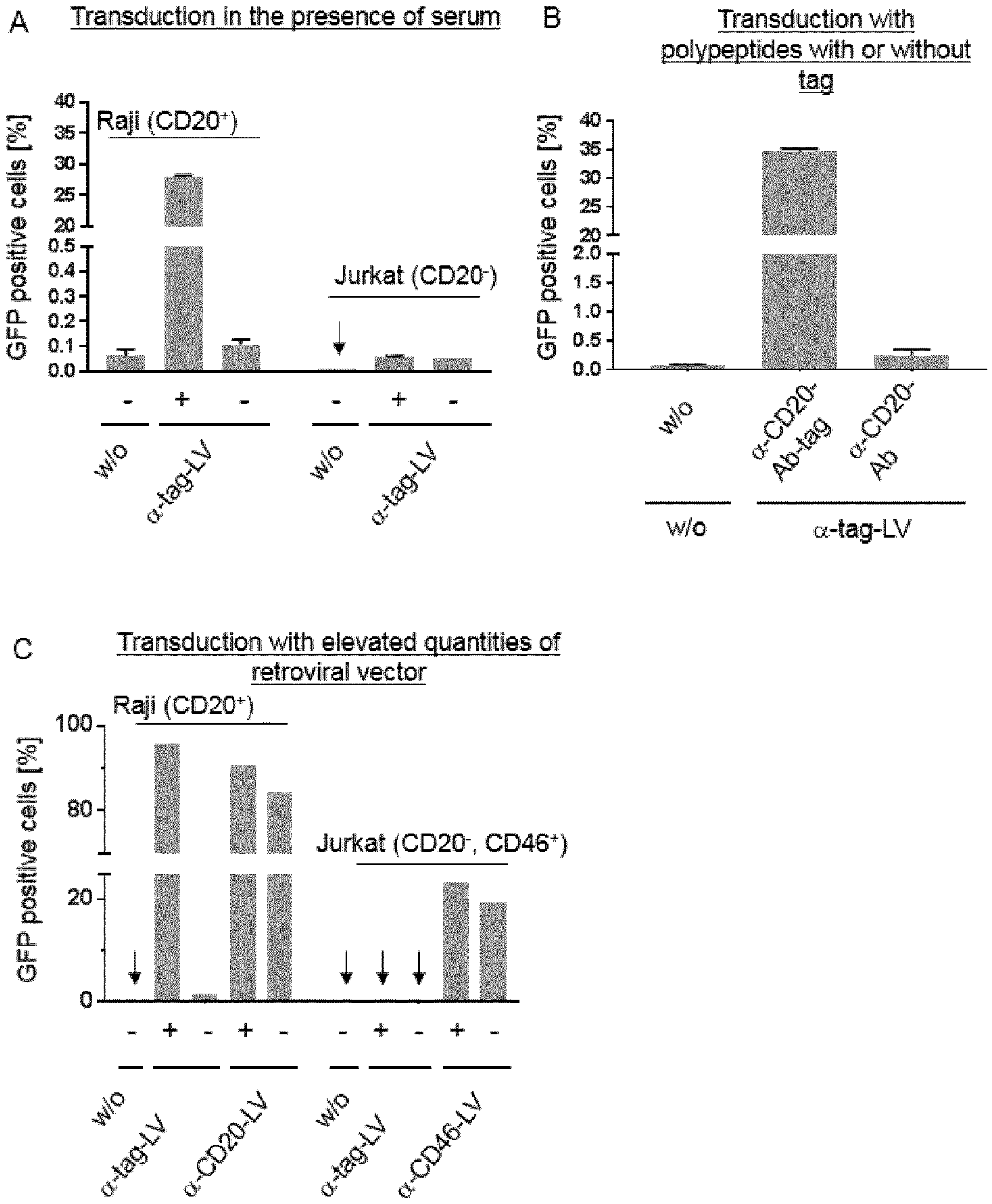
FIG 9A-C

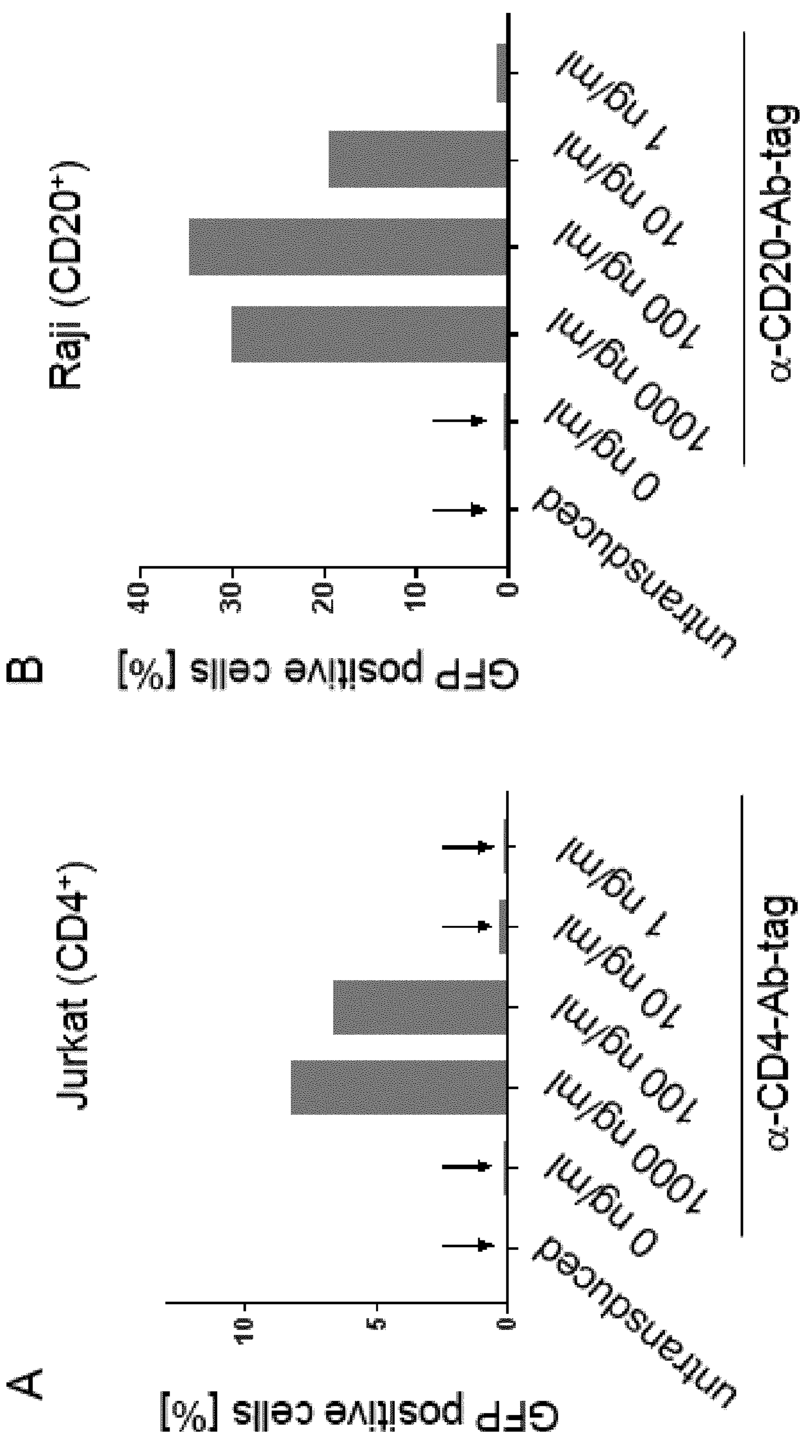
FIG 10A-B

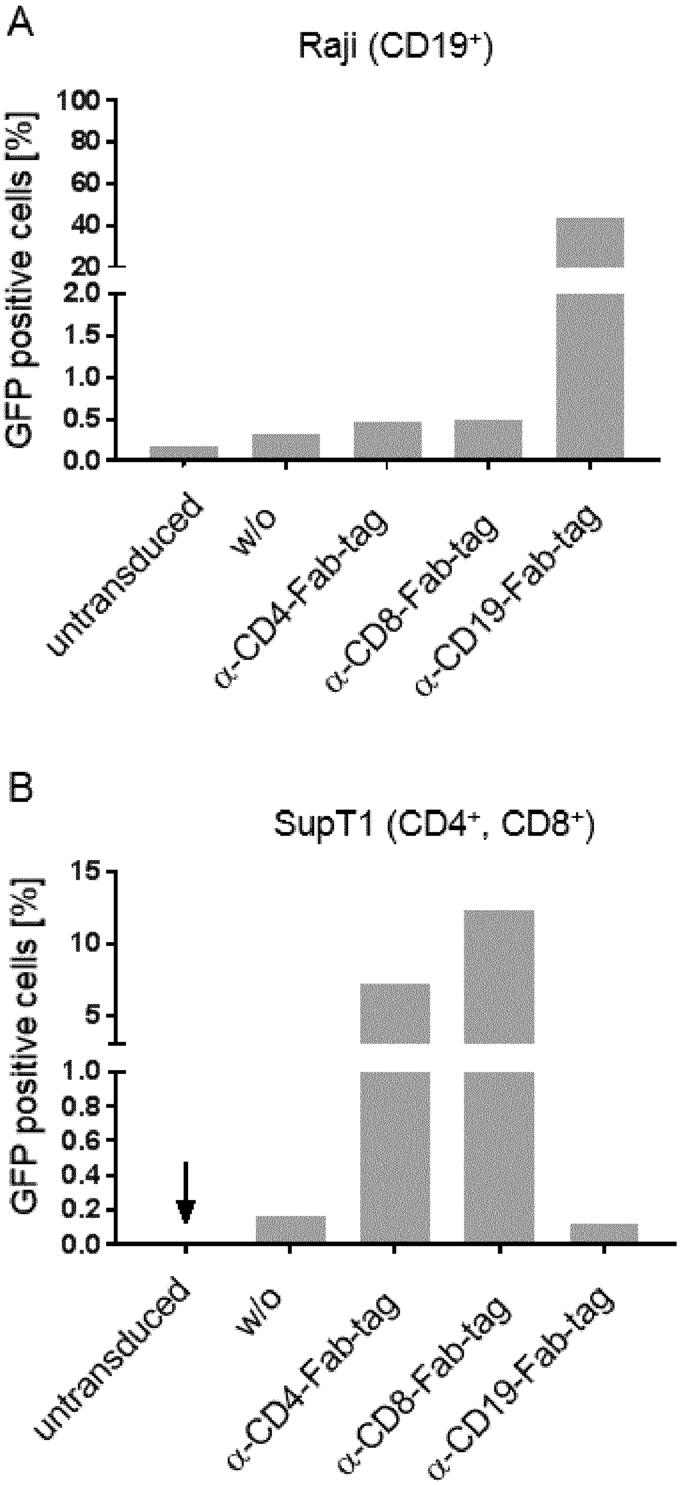
FIG 11A-B

SEQUENCE LISTING

```
<160> NUMBER OF SEQ ID NOS: 15

<210> SEQ ID NO 1
<211> LENGTH: 122
<212> TYPE: PRT
<213> ORGANISM: Artificial sequence
<220> FEATURE:
<223> OTHER INFORMATION: Biotin AB heavy chain

<400> SEQUENCE: 1

Glu Val Gln Leu Val Glu Ser Gly Gly Gly Leu Val Lys Pro Gly Gly
1               5                   10                  15

Ser Leu Lys Leu Ser Cys Ala Val Ser Gly Phe Thr Phe Ser Asn Tyr
            20                  25                  30

Ala Met Ser Trp Val Arg Gln Thr Pro Glu Thr Arg Leu Asn Trp Val
        35                  40                  45

Ala Thr Ile Thr Gly Gly Gly Ser Tyr Thr Tyr Tyr Pro Asp Ser Val
    50                  55                  60

Lys Gly Arg Phe Thr Ile Ser Arg Asp Asn Ala Lys Asp Thr Leu Tyr
65                  70                  75                  80

Leu Gln Met Ser Ser Leu Arg Ser Glu Asp Thr Ala Met Tyr Tyr Cys
                85                  90                  95
```

```
Val Arg Gln Arg Val Gly Asp Tyr Val Ser Ser Leu Leu Gly Tyr Trp
            100                 105                 110

Gly Gln Gly Thr Leu Val Thr Val Ser Ala
        115                 120


<210> SEQ ID NO 2
<211> LENGTH: 112
<212> TYPE: PRT
<213> ORGANISM: Artificial sequence
<220> FEATURE:
<223> OTHER INFORMATION: Biotin AB light chain

<400> SEQUENCE: 2

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Phe Leu Gln Lys Pro Gly Gln Ser
        35                  40                  45

Pro Asn Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Tyr Thr Phe Gly Gly Gly Thr Lys Leu Glu Ile Lys
            100                 105                 110


<210> SEQ ID NO 3
<211> LENGTH: 5
<212> TYPE: PRT
<213> ORGANISM: Artificial sequence
<220> FEATURE:
<223> OTHER INFORMATION: measles virus (Edmonston strain); transmembrane
      domain of F protein

<400> SEQUENCE: 3

Leu Ile Cys Cys Cys
1               5


<210> SEQ ID NO 4
<211> LENGTH: 4
<212> TYPE: PRT
<213> ORGANISM: Artificial sequence
<220> FEATURE:
<223> OTHER INFORMATION: measles virus (Edmonston strain); transmembrane
      domain of H protein

<400> SEQUENCE: 4

Pro Tyr Val Leu
1


<210> SEQ ID NO 5
<211> LENGTH: 33
<212> TYPE: PRT
<213> ORGANISM: Artificial sequence
<220> FEATURE:
<223> OTHER INFORMATION: measles virus (Edmonston strain); cytoplasmic
      domain of F protein

<400> SEQUENCE: 5

Arg Gly Arg Cys Asn Lys Lys Gly Glu Gln Val Gly Met Ser Arg Pro
1               5                   10                  15
```

-continued

```
Gly Leu Lys Pro Asp Leu Thr Gly Thr Ser Lys Ser Tyr Val Arg Ser
            20                  25                  30

Leu


<210> SEQ ID NO 6
<211> LENGTH: 34
<212> TYPE: PRT
<213> ORGANISM: Artificial sequence
<220> FEATURE:
<223> OTHER INFORMATION: measles virus (Edmonston strain); cytoplasmic
      domain of H protein

<400> SEQUENCE: 6

Met Ser Pro Gln Arg Asp Arg Ile Asn Ala Phe Tyr Lys Asp Asn Pro
1               5                   10                  15

His Pro Lys Gly Ser Arg Ile Val Ile Asn Arg Glu His Leu Met Ile
            20                  25                  30

Asp Arg


<210> SEQ ID NO 7
<211> LENGTH: 21
<212> TYPE: PRT
<213> ORGANISM: Artificial sequence
<220> FEATURE:
<223> OTHER INFORMATION: Nipah Virus; transmembrane domain of G protein

<400> SEQUENCE: 7

Phe Asn Thr Tyr Ile Ala Leu Leu Gly Ser Ile Val Ile Ile Val Met
1               5                   10                  15

Asn Ile Met Ile Ile
            20


<210> SEQ ID NO 8
<211> LENGTH: 45
<212> TYPE: PRT
<213> ORGANISM: Artificial sequence
<220> FEATURE:
<223> OTHER INFORMATION: Nipah Virus; cytoplasmic domain of G protein

<400> SEQUENCE: 8

Met Pro Ala Glu Asn Lys Lys Val Arg Phe Glu Asn Thr Thr Ser Asp
1               5                   10                  15

Lys Gly Lys Ile Pro Ser Lys Val Ile Lys Ser Tyr Tyr Gly Thr Met
            20                  25                  30

Asp Ile Lys Lys Ile Asn Glu Gly Leu Leu Asp Ser Lys
        35                  40                  45


<210> SEQ ID NO 9
<211> LENGTH: 21
<212> TYPE: PRT
<213> ORGANISM: Artificial sequence
<220> FEATURE:
<223> OTHER INFORMATION: Nipah Virus; transmembrane domain of F protein

<400> SEQUENCE: 9

Tyr Val Leu Ser Ile Ala Ser Leu Cys Ile Gly Leu Ile Thr Phe Ile
1               5                   10                  15

Ser Phe Ile Ile Val
            20


<210> SEQ ID NO 10
<211> LENGTH: 28
<212> TYPE: PRT
```

<213> ORGANISM: Artificial sequence
<220> FEATURE:
<223> OTHER INFORMATION: Nipah Virus; cytoplasmic domain of F protein

<400> SEQUENCE: 10

```
Glu Lys Lys Arg Asn Thr Tyr Ser Arg Leu Glu Asp Arg Arg Val Arg
1               5                   10                  15

Pro Thr Ser Ser Gly Asp Leu Tyr Tyr Ile Gly Thr
            20                  25
```

<210> SEQ ID NO 11
<211> LENGTH: 15
<212> TYPE: PRT
<213> ORGANISM: Artificial sequence
<220> FEATURE:
<223> OTHER INFORMATION: scFV linker sequence

<400> SEQUENCE: 11

```
Gly Gly Gly Gly Ser Gly Gly Gly Gly Ser Gly Gly Gly Gly Ser
1               5                   10                  15
```

<210> SEQ ID NO 12
<211> LENGTH: 6
<212> TYPE: PRT
<213> ORGANISM: Artificial sequence
<220> FEATURE:
<223> OTHER INFORMATION: HIS tag sequence

<400> SEQUENCE: 12

```
His His His His His His
1               5
```

<210> SEQ ID NO 13
<211> LENGTH: 117
<212> TYPE: PRT
<213> ORGANISM: Artificial sequence
<220> FEATURE:
<223> OTHER INFORMATION: Dextran AB heavy chain

<400> SEQUENCE: 13

```
Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Asp Ile Asn Pro Asn Asn Gly Gly Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Pro Tyr Tyr Tyr Thr Ser Ser Leu Val Trp Gly Thr Gly Thr Thr
            100                 105                 110

Val Thr Val Ser Ala
        115
```

<210> SEQ ID NO 14
<211> LENGTH: 106
<212> TYPE: PRT
<213> ORGANISM: Artificial sequence
<220> FEATURE:
<223> OTHER INFORMATION: Dextran AB light chain -continued

```
<400> SEQUENCE: 14

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys
            100                 105


<210> SEQ ID NO 15
<211> LENGTH: 26
<212> TYPE: PRT
<213> ORGANISM: Artificial sequence
<220> FEATURE:
<223> OTHER INFORMATION: Vectofusin

<400> SEQUENCE: 15

Lys Lys Ala Leu Leu Ala Leu Ala Leu His His Leu Ala His Leu Ala
1               5                   10                  15

Leu His Leu Ala Leu Ala Leu Lys Lys Ala
            20                  25
```

ADAPTER-BASED RETROVIRAL VECTOR SYSTEM FOR THE SELECTIVE TRANSDUCTION OF TARGET CELLS

REFERENCE TO RELATED APPLICATIONS

This is the U.S. National Stage of international patent application PCT/EP2018/079486, published on May 9, 2019 with publication number WO 2019/086351. The PCT application is hereby incorporated herein by reference its entirety for all purposes.

FIELD OF THE INVENTION

The present invention relates to the field of pseudotyped retroviral vector particles or vector-like particles (VLP) thereof, having specificity for a tag wherein said tag is coupled to a polypeptide that binds to an antigen expressed on a target cell, thereby allowing targeted transduction of multiple target cell moieties with said retroviral vector particles or vector-like particles thereof.

BACKGROUND OF THE INVENTION

Gene delivery using retroviral vectors is a widely-used approach to correct defective genes and provide new functions to cells. However, due to the nature of the commonly used type of retroviral vectors, they are not selective by design, which hampers the safety profile and applicability of retroviral vectors in many therapeutic fields.

Usually, retroviral vectors are pseudotyped with the envelope protein of the Vesicular Stomatitis Virus (VSV-G). This pseudotype transduces a broad range of target cells including therapeutic relevant cell types but it may require preactivation with stimulatory agents to reach sufficient transduction efficiency levels.

Moreover, in mixed cell populations selection procedures like magnetic cell sorting are required to express the target gene in the defined cell type only. Thereby, transduction of the off-target population resulting in potential side effects are avoided.

Alternatively, attempts at designing LV systems that are selective by design and thus do not require preselection of the target population were tested. However, these systems are limited in terms of selectivity, productivity or applicability.

US20160333374 describes a system that is based on antibody fragments like scFVs that were fused to the ectodomain of VSV-G (VSVG-scFV). The goal was to combine the favorable productivity of VSV-G and the specificity of scFVs. This approach enabled binding to the target antigen but VSVG-scFV was unable to mediate fusion of the retroviral with target cell membrane—and in consequence—also transduction. To overcome this hurdle, unmodified VSV-G had to be co-displayed with VSVG-scFV. Consequently, the co-display of functional but nonselective VSV-G with selective but non-functional VSV-G-scFV only led to a preferential transduction of target antigen expressing cells. But most importantly, cells not expressing the target antigen were transduced as well due to the retained function of the (non-selective) native VSV-G. Thus, this system favors transduction of target-antigen expressing cells but is not truly selective.

Higher selectivity was seen with retargeted lentiviral vectors pseudotyped with measles virus envelope proteins (MV-LV) comprising a protein with fusion activity (F protein) and a protein with antigen-binding activity (H protein) that has been fused to a scFV (WO2008/037458A2). The broad application of this system has been tested for a variety of antigens in vitro but also in vivo (Anliker et al. (2010)). However, for each specificity of targeted retroviral vectors a separate retroviral production is required. Thus, this system does not allow full flexibility of the specificity of the retroviral vector. Also, controlling the transduction efficiency on the targeted cell population thereby, for example, controlling the expression rate of the gene of interest by the integrated vector copy number (VCN) is limited.

Not only lentiviral vectors were successfully pseudotyped with truncated measles virus envelope proteins but also gammaretroviral vectors (Edes (2016), Frecha et al. (2008)). Interestingly, in the context of gammaretroviral vectors the highest retroviral vector titer was measured with slightly different truncation variants as compared to the variants tested for pseudotyping of lentiviral vectors. Although these systems are functional some technical drawbacks have been observed. For example, retroviral vector titers are highly dependent on the surface expression levels of the chimeric H-scFV protein during production (i.e. upon transfection of HEK-293T cells). Particularly, the sequence of the framework region of the scFV has been shown to influence the biophysical properties of the displayed scFVs and in consequence the functional retroviral vector titer (Friedel et al. (2015)).

Bender et al. (2016), Khetawat and Broder (2010) and U.S. Pat. No. 9,486,539B2 have also shown that envelope proteins derived from another Paramyxoviridae virus, the Nipah virus, may be used to pseudotype lentiviral vectors as well and optionally retarget it for selective transduction. Interestingly, Rasbach et al. (2013) added a non-viral transmembrane protein with antigen binding function to MV-LV so that 3 different membrane proteins were used for pseudotyping. Using this approach the attachment function of measles H protein was replaced by the non-viral transmembrane protein, but the fusion helper function of measles H protein was still needed to yield functional pseudotyped lentiviral vectors. The addition of another membrane protein increased the functional lentiviral vector titer about one order of magnitude compared to lentiviral vectors pseudotyped with only 2 envelope proteins.

However, one main drawback remains for all pseudotyped retroviral vector systems that have been described before: for each specificity of targeted retroviral vectors a separate retroviral production is required as different envelope protein constructs have to be used. Production of pseudotyped retroviral vectors is not only laborious and costly, but also requires lot-wise QC testing to determine the functional retroviral vector titer. In addition, these systems do not provide highly flexible solutions to instantly change the specificity of the pseudotyped retroviral vector nor do they enable control over the transduction efficiency to adjust to the actual need of the particular application. From a safety point of view, control over the integrated vector copy numbers genomes is desired especially in a clinical setting, where upper limits of the VCN are discussed.

Alternatively, generic adapter-based systems were developed in the art with universal retroviral vectors that were rendered to be selective by adding engineered polypeptides specific for the antigen of choice (reviewed in Metzner et al. (2013)). For example, Roux et al. (1989) describes an adapter based system in the context of gammaretroviral vectors that is based on bispecific antibody complexes. One biotinylated antibody specific for a gammaretroviral particle was coupled via avidin to another biotinylated antibody specific for the target antigen of choice expressed by target cells. However, the authors noticed low transduction yields and hypothesized that the specificity tested or the antibody complex itself could account for the limited efficiency that has been observed.

Snitkovsky et al. (2002) provides an alternative system that is based on retroviral vectors that bind to recombinant adapter molecules consisting of extracellular receptor domains fused to antigen binding ligands like scFVs. Here, again very limited efficiencies with up to 5% transduced target cells were observed.

Morizono et al. (2009) developed lentiviral vectors presenting a protein A domain binding specifically to the Fc portion of an antibody used as adapter molecule. Because the affinity of Fc to protein A is low, biotin avidin interaction was also evaluated. Biotin was added to an viral envelope protein via an inserted bacterial biotin adaptor peptide (BAP). Here, avidin-conjugated IgGs were used as adapter. However, avidin also binds to charged cell surface molecules. Therefore, as a consequence, avidin-conjugated antibodies may also bind unspecifically to non-target cells which limits its applicability.

Kaikkonen et al. (2009) also used biotin avidin interaction to specifically transduce target cells with adapter molecules. This time, avidin displaying retroviral vectors were applied to biotinylated ligands or antibodies. Avidin was added to a transmembrane anchor of VSV-G for efficient incorporation (Avidin-VSVG). As this recombinant envelope protein promotes only binding but not fusion anymore gp64 derived from Baculovirus was co-expressed on the surface of the retroviral vector. Kaikkonen et al. (2009) chose adapters specific for receptors overexpressed on tumor cells (transferrin receptor, EGFR and CD46). This system was not truly selective because gp64 is co-displayed on the retroviral vector envelope along with Avidin-VSVG. The addition of the adapter enhanced transduction of target cell population but unspecific transduction has been detected as well. Unspecific transduction is especially critical for all adaptable retroviral vector systems that use biotin interaction. Biotin-specific retroviral vectors may bind to naturally occurring biotin present on the cell surface which induces unspecific transduction of these cells. Vice versa, adapter molecules specific for biotin may also bind to naturally occurring biotin present on non-target cells.

Hoop (2014) used lentiviral vectors pseudotyped with measles virus envelope proteins (MV-LV) to develop an adapter based retroviral vector system. This time the truncated H protein variant recognizing the native receptor was used (i.e. no scFV). The adapter was designed in such way that the lentiviral vector binding domain is an extracellular portion of a measles virus receptor (CD46). The soluble receptor fragment was fused to a target cell antigen binding region via a flexible (G4S)3 linker. Surprisingly, it was found that the adapter rendered the pseudotyped LV particle to be non-selective: i.e. the transduction efficiency not only on the target cell population was elevated but also on the non-target population not expressing the target antigen of the adapter. The effect of this adapter is comparable to commonly known transduction enhancement reagents like Polybrene®, Protaminesulfate or Vectofusin-1®. But the mode of action of these reagents is to overcome charge repulsion of viral and target cell membrane, bringing both membranes in close proximity and elevate transduction efficiency levels and gene transfer rates.

Thus, the technologies described in the art show results in terms of either selectivity, control or applicability but none of these systems provide solutions addressing all of these parameters in combination.

In conclusion, there is a need in the art for an alternative and/or improved transduction technology in the field of pseudotyped retroviral vectors or virus like particles thereof such as a method that addresses the above-mentioned parameters in combination and allow a controlled and selective transduction of target cells with pseudotyped retroviral vectors or virus-like particles thereof and may be applied clinically.

SUMMARY OF THE INVENTION

The inventors surprisingly found that retroviral vector particles or virus-like particles thereof pseudotyped with Paramyxoviridae virus envelope proteins, that have antigen-binding and fusion activity and wherein said protein having antigen binding activity is a chimeric protein that does not interact with at least one of its native receptors can be used to generate adaptable retroviral vector particles or virus-like particles thereof systems with high target cell selectivity.

This finding is surprising because an alternative approach that was also based on Paramyxoviridae derived envelope proteins for pseudotyping, clearly demonstrated that such pseudotyped, retroviral vectors are transducing non-selectively in the presence of an adapter (Hoop, 2014).

In one embodiment of the present invention, an adaptable retroviral vector or virus-like particles thereof system is provided that also uses biotin interaction to bind to the adapter molecule, wherein the adapter molecule comprises a polypeptide, e.g. an antibody that binds to an antigen of a target cell, that is coupled to biotin via a specific linker. The envelope protein of the retrovirus as disclosed herein binds with higher preference the biotin of the adapter molecule than free biotin or biotin coupled in another manner to a moiety such as a polypeptide. Therefore, in contrast to alternative systems of the prior art there is no or less competition with naturally occurring biotin, thereby avoiding e.g. limited or unspecific transduction.

The finding of the present invention makes use of "universal" retroviral vectors that are more efficiently produced at large scale. By adjusting the amount and the specificity of the adapter the user gains full control over the transduction process in a tunable manner on the target cells only.

For example, a recombinant truncated H protein version that does not interact with its native receptors CD46, Nectin-4 and/or SLAM (by introducing well-known mutations into the truncated H protein) together with a polypeptide comprising an antigen binding domain is created, wherein said polypeptide is specific for a tag of a tagged polypeptide and wherein said tagged polypeptide binds specifically to an antigen expressed on the surface of a target cell. Therefore, the adaptable system of retroviral vector particle or virus-like particles thereof as disclosed herein comprises the retroviral vector particle or virus-like particle thereof and the corresponding tagged polypeptide as disclosed herein.

For example, the truncated F protein is mediating the fusion of the viral membrane and the cellular membrane of the target cell. The truncated H protein supports the fusion function but does not interact with its native receptors CD46, Nectin-4 or SLAM anymore as it is blinded by the introduction of the mutations. The part of the chimeric protein that comprises the polypeptide comprising an antigen binding domain specifically binds a tag of a tagged polypeptide. The tag may be a dextran, a hapten such as FITC and biotin or a linker/label epitope (LLE) of a target cell binding molecule (TCBM) as disclosed herein. The tagged polypeptide may be e.g. a haptenylated antibody or antigen binding fragment thereof that binds specifically an antigen that is expressed on the surface of a target cell, e.g. a biotinylated antibody specific for the antigen of choice.

The retroviral vector particle or virus-like particles thereof as disclosed herein thus enter those cells expressing the corresponding marker (antigen) bound by the antigen-binding domain of the tagged polypeptide, wherein the retroviral vector particle or virus-like particles thereof binds to the tag of the tagged polypeptide via the polypeptide comprising the antigen-binding domain specific for the tag of the truncated receptor binding protein, e.g. the H protein of the retroviral vector particle; however, the transduction is impaired on cells not expressing these markers (antigen).

Likewise, retroviral vector particles or virus-like particles thereof as disclosed herein, can transduce target cells expressing the corresponding marker only in the presence of said polypeptide. In the absence of said polypeptide the transduction of said retroviral vectors particles or virus-like particles thereof is impaired on any cell type.

Therefore, cell entry and transduction using the retroviral vector particle or virus-like particles thereof of the present invention demonstrated to be an efficient and effective means for highly selective gene transfer into specific cells in an adaptable manner. In one embodiment of the invention such target cells are selected from the group consisting of immune cells, hematopoietic cells, stem cells, cancerous cells, cells of the nervous system, muscle cells, endothelial progenitor cells (EPCs), endothelial cells and diseased cells.

Pharmaceutical compositions based on the retroviral vector particle or virus-like particles thereof and the corresponding tagged polypeptide(s) of the present invention may be formulated in any conventional manner using one or more physiologically acceptable carriers or excipients. Thus, the retroviral vector particle or virus-like particles thereof of the present invention may be formulated for administration (together with the tagged polypeptide or subsequently) by, for example, injection, inhalation or insulation (either through the mouth or the nose) or by oral, buccal, parenteral or rectal administration.

The retroviral vector particle or virus-like particles thereof and the tagged polypeptide of the present invention may be administered separately or already conjugated. The separate administration of the retroviral vector particle or virus-like particles thereof and the tagged polypeptide of the present invention may occur either simultaneously or subsequently. The retroviral vector particle or virus-like particles thereof and the tagged polypeptide of the present invention may be administered only once or multiple times.

The retroviral vector particle or virus-like particles thereof of the present invention may be administered first followed by the administration of the tagged polypeptide or vice versa.

Such pharmaceutical compositions may be useful for transducing specifically target cells, which can include, inter alia, an immune cell, a cancerous cell or a stem cell, with the gene product of a desired protein that, if expressed in the targeted cell, leads to the prevention or the treatment of a particular medical condition.

A Retroviral vectors are pseudotyped with envelope proteins responsible for antigen binding (A) and fusion (F). A is modified so that it cannot interact with at least one of its native receptors as depicted by the shield. To restore antigen binding, A is fused at its ectodomain to a polypeptide comprising an antigen binding domain like scFV. It is specific for a tag of a tagged polypeptide (adapter) and the antigen binding domain of the adapter molecule binds to the antigen expressed on the target cell inducing fusion and transduction.

B Adapter mediated transduction with measles virus envelope proteins. The H protein (H) has been mutated so that it cannot interact with its native receptors CD46 and SLAM as depicted by the shield. An antigen binding domain, like a scFV specific for a tag, has been added to mutated H. The adapter molecule is comprised of a biotinylated antibody specific for an antigen expressed by the target cell. The tag comprises biotin. The transduction efficiency was determined 72 h post transduction by quantification of the GFP positive cells using flow cytometry.

C Different domains of the adapter molecule are depicted.

Figure 2:
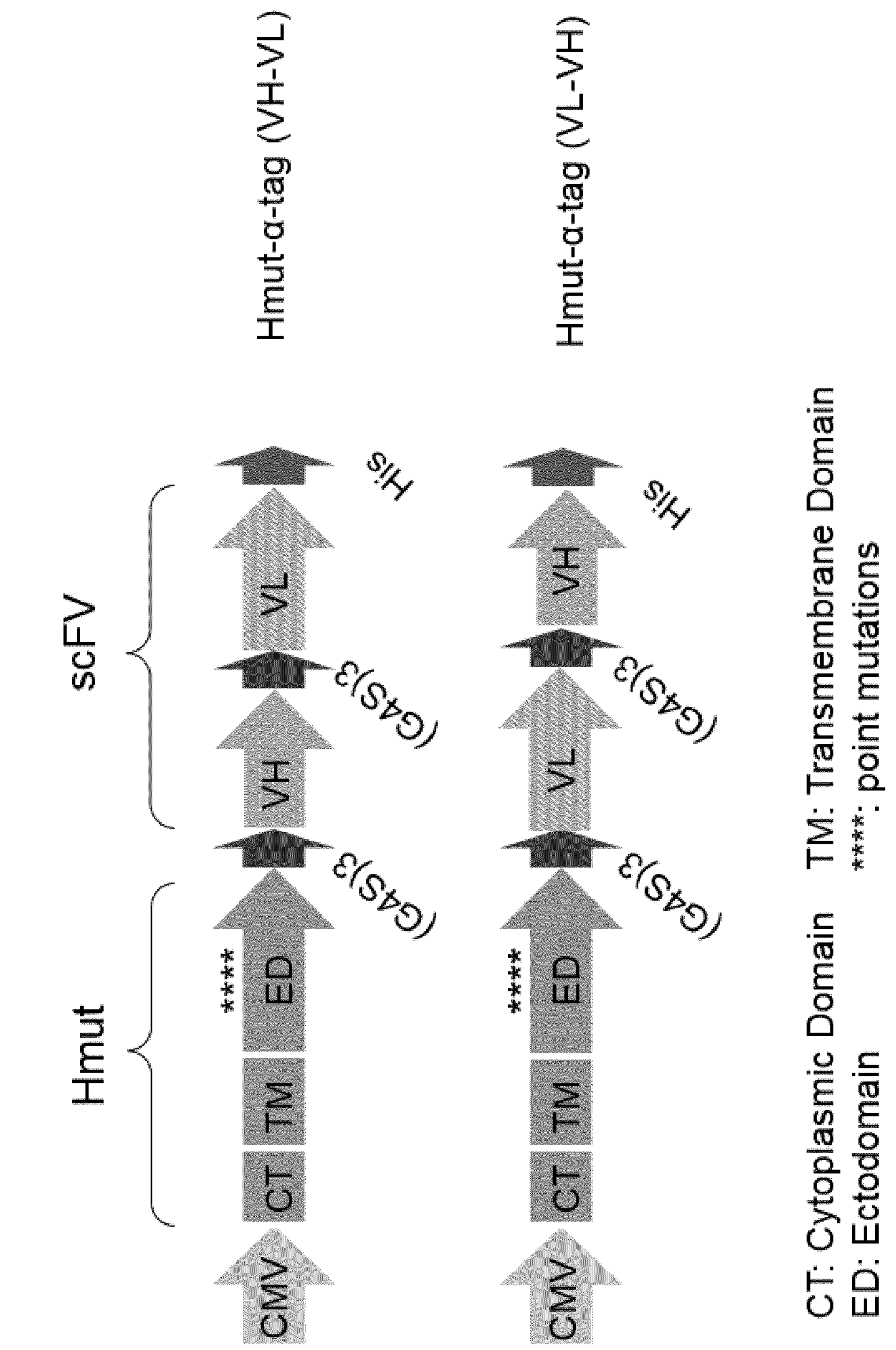

FIG. 2: Schematic representation of the construct Hmut-α-tag Genetic elements encoding the construct Hmut-α-tag including a scFV specific for a tag with variable domains in two different orientations (VH-VL or VL-$V_H$). The protein is expressed under a CMV promotor followed by a H protein encoding sequence that has been mutated at four positions (depicted as asterix) so that interaction with its native receptors CD46 and SLAM is no longer possible (Hmut). The H protein and the scFV are linked via a (G4S)3 linker. The variable domains are connected via a (G4S)3 linker as well. A His tag is included for detection purposes.

FIG. 3: Expression levels of Hmut-α-tag and binding to a tagged polypeptide HEK-293T cells were left untransfected or were transfected with plasmids encoding Hmut-α-tag (VH-VL) or Hmut-α-tag (VL-VH).

A Surface expression of Hmut-α-tag as determined by flow cytometry two days post transfection upon staining with α-His antibodies.

B Binding of Hmut-α-tag to a tagged polypeptide was measured two days post transfection using a fluorescently labeled and tagged α-CD25 antibody.

FIG. 4: Quantification of retroviral vector titers pseudotyped with Hmut-α-tag A A titration method for α-tag-LV was developed without tagged polypeptide to avoid variations that may occur, for example, due to different adapter formats or for different specificities of the adapter. HT1080 cells were biotinylated using Biotin-LC-LC-NHS leading in a random biotinylation of all cell surface proteins. Successful biotinylation was confirmed by staining with α-biotin antibodies (left). Biotinylated cells were then transduced with defined volumes of α-tag-LV encoding GFP. Three days post transfection the ratio of GFP positive cells indicates successful transduction as measured by flow cytometry (right). An example of the gating strategy is shown.

B Screening titers of concentrated α-CD46-LV on HT1080 cells, concentrated α-CD20-LV on HT1080-CD20 and concentrated α-tag-LV on biotinylated HT1080 cells.

FIG. 5: Impact of the order of adding GFP-encoding retroviral vector (α-tag-LV, α-CD20-LV or α-CD46-LV), polypeptide α-CD20-Ab-tag (biotinylated antibody specific for CD20) and target cells (Raij (CD20 & CD46 positive) or Jurkat as control (CD20 negative, CD46 positive)) on transduction efficiency. Retroviral vector was added at a MOI 0.05. 72 h post transduction the transduction efficiency was determined by flow cytometry determining the ratio of GFP positive cells.

A Lentiviral vectors were incubated in the absence (−) or presence (+) of the tagged polypeptide for 30 min at 4° C. Subsequently, the preincubated LV/α-CD20-Ab-tag mixture was added to cells or the cells were left untransduced (w/o).

B Raji and Jurkat cells were preincubated in absence (−) or presence (+) of α-CD20-Ab-tag for 30 min at 4° C. The preincubated cell/α-CD20-Ab-tag mixture was left untransduced or transduced.

C Raji and Jurkat cells were preincubated with lentiviral vector for 30 min at 37° C. or without retroviral vector (w/o). Subsequently, α-CD20-Ab-tag was added (+) or not supplemented (−).

FIG. 6: Evaluation of transduction enhancement reagents in terms of selectivity and transduction efficiency. Raji (CD20 and CD46 positive) or Jurkat cells (CD20 negative, CD46 positive) were preincubated with (+) or without (−) the polypeptide α-CD20-Ab-tag for 30 min at 4° C. followed by the addition of α-tag-LV, α-CD20-LV or α-CD46-LV (MOI=0.05). The tagged polypeptide was a biotinylated antibody and the used tag comprises biotin. The transduction efficiency was determined 72 h post transduction by quantification of the GFP positive cells using flow cytometry.

A No transduction enhancement reagent was added.

B Polybrene® was added as transduction enhancer.

C Vectofusin-1® was added as transduction enhancer.

FIG. 7: Expanding the specificities of the tagged polypeptide to CD4, CD8, CD19, CD20 and CD46. Target cells expressing or not expressing the target antigen were incubated in absence (−) or presence (+) of the polypeptide α-CD4-Ab-tag, α-CD8-Ab-tag, α-CD19-Ab-tag, α-CD20-Ab-tag or α-CD46-Ab-tag, respectively, for 30 min at 4° C. The tagged polypeptide was a biotinylated antibody and the used tag comprises biotin. GFP encoding α-tag-LV was applied at a MOI of 0.05 in the presence of Vectofusin-1®. Three days post transduction the cells were stained with antibodies specific for the same antigen as the used tagged polypeptide and the transduction efficiency was determined by quantification of GFP positive cell using flow cytometry. For transductions of cells expressing the corresponding antigen of the tagged polypeptide, the transduction rate refers to all cells expressing the target antigen. For transductions of cells not expressing the corresponding antigen of the tagged polypeptide, the transduction rate refers to all cells not expressing the target antigen.

A SupT1 cells (positive for CD4, CD8 and CD46; negative for CD19 and CD20) were used.

B Jurkat cells (positive for CD4 and CD46 positive; negative for CD8, CD19 and CD20) were used C HT1080 cells (positive for CD46, negative for CD4, CD8, CD19, CD20)

D Raji cells (positive for CD19, CD20 and CD46; negative for CD4 and CD8)

Figure 8A:
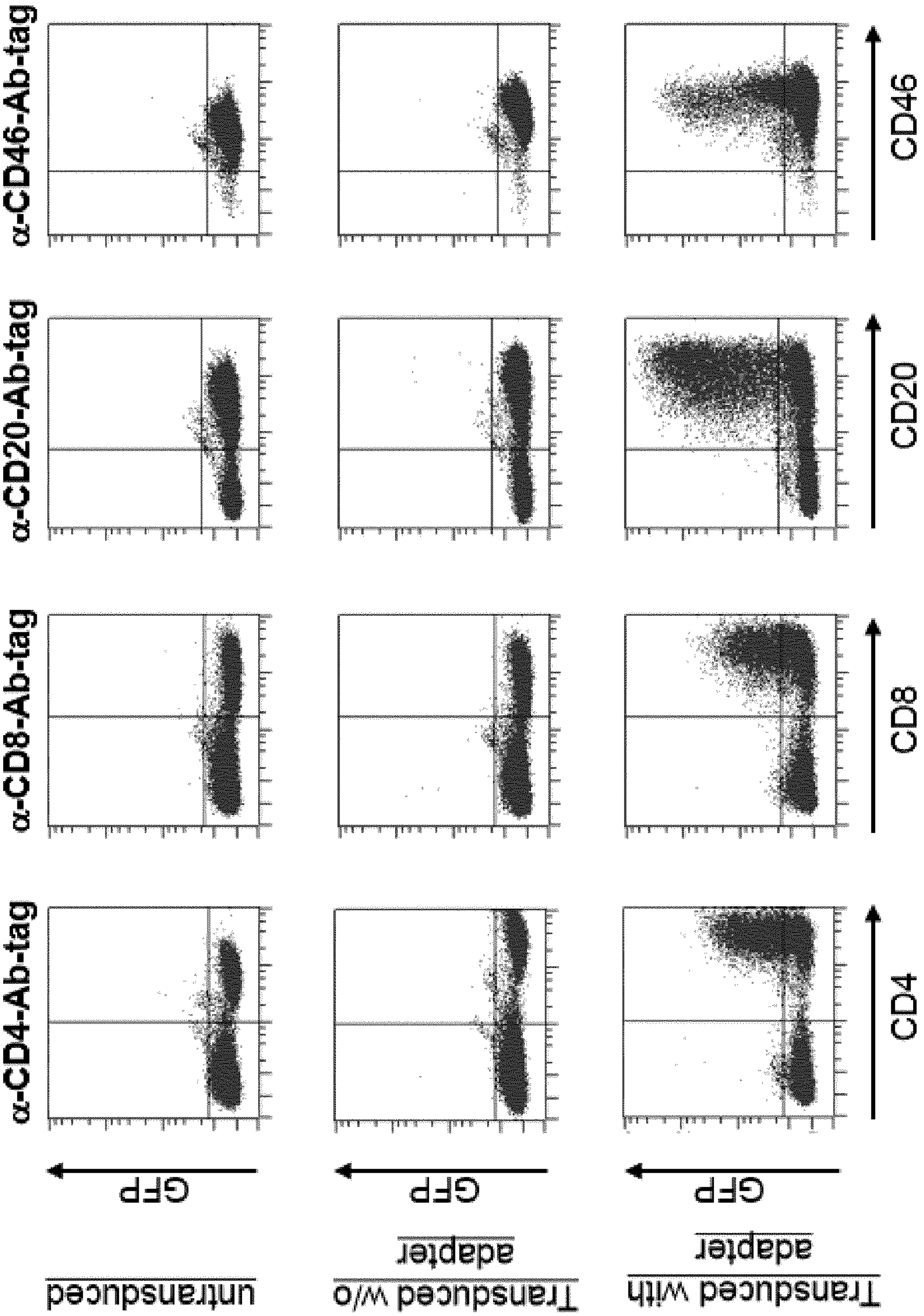

FIG. 8: Selectivity in mixed cell populations with cells expressing the target antigen and cells not expressing the target antigen. The tagged polypeptide was a biotinylated antibody and the used tag comprises biotin. Raji cells (positive for CD19, CD20 and CD46; negative for CD4 and CD8) were mixed in equal parts with SupT1 cells (positive for CD4, CD8 and CD46; negative for CD19 and CD20).

A Co-cultured cells were transduced with GFP encoding α-tag-LV (MOI=0.05, including Vectofusin-1®) in the presence (Transduced with adapter) or absence (Transduction w/o adapter) of the tagged polypeptide specific for the antigen as indicated at the top. As control, co-cultured cells were left untransduced. Three days post transduction the cells were stained with antibodies specific for the same antigen as tagged polypeptide and the transduction efficiency was determined by quantification of GFP positive cells using flow cytometry.

B Quantification of the flow cytometric data of A. The rate of GFP negative and GFP positive cells is shown separately for cells not expressing or for cells expressing the target antigen of the tagged polypeptide.

FIG. 9: Selectivity under conditions prone to induce unspecific transduction.

The tagged polypeptide was a biotinylated antibody and the used tag comprises biotin. Three 15 days post transduction the transduction efficiency was determined by quantification of GFP positive cells using flow cytometry.

A Transduction in the presence of serum. CD20 positive Raij cells and CD20 negative Jurkat cells were transduced with Vectofusin-1® in medium supplemented with 10% FCS with GFP encoding α-tag-LV (MOI 0.05) in the presence (+) or absence (−) of the polypeptide α-CD20-Ab-tag.

B Transduction with polypeptides with or without tag. CD20 positive Raij cells were transduced with Vectofusin-1® with GFP encoding α-tag-LV (MOI 0.05) with the polypeptide α-CD20-Ab-tag or α-CD20-Ab.

C Transduction with elevated quantities of retroviral vector. Raji cells (CD20 and CD46 positive) and Jurkat cells (CD20 negative, CD46 positive) were either left untransduced (w/o) or were transduced with Vectofusin-1® at a MOI of 0.4 either with α-tag-LV, α-CD20-LV or α-CD46-LV in the presence (+) or absence (−) of α-CD20-Ab-tag.

FIG. 10: Titration of the tagged polypeptide to determine the optimal adapter molecule concentration. The tagged polypeptide was a biotinylated antibody and the used tag comprises biotin. Three days post transduction the transduction efficiency was determined by quantification of GFP positive cells using flow cytometry.

A Jurkat cells (CD4 positive, low expression) were transduced with GFP encoding α-tag-LV with Vectofusin-1® at a MOI of 0.05 in the presence of the tagged polypeptide α-CD4-Ab-tag at indicated concentrations.

B Raji (CD20 positive, high expression) cells were transduced with GFP encoding α-tag-LV with Vectofusin-1® at a MOI of 0.05 with α-CD20-Ab-tag at indicated concentrations.

FIG. 11: Evaluation of an alternative adapter format: tagged fragments of antibodies (Fabs).

The tagged polypeptide was a biotinylated Fab fragment and the used tag comprises biotin. Three days post transduction the transduction efficiency was determined by quantification of GFP positive cells using flow cytometry.

A CD19 positive Raji cells were transduced with GFP encoding α-tag-LV with Vectofusin-1® at a MOI of 0.05 in the absence (w/o) or presence of 1 μg/ml tagged α-CD4-Fab-tag, α-CD8-Fab-tag or α-CD19-Fab-tag.

B CD4 and CD8 positive SupT1 cells were transduced with GFP encoding α-tag-LV with Vectofusin-1® at a MOI of 0.05 in the absence (w/o) or presence of 1 μg/ml α-CD4-Fab-tag, α-CD8-Fab-tag or α-CD19-Fab-tag.

Figure 12:
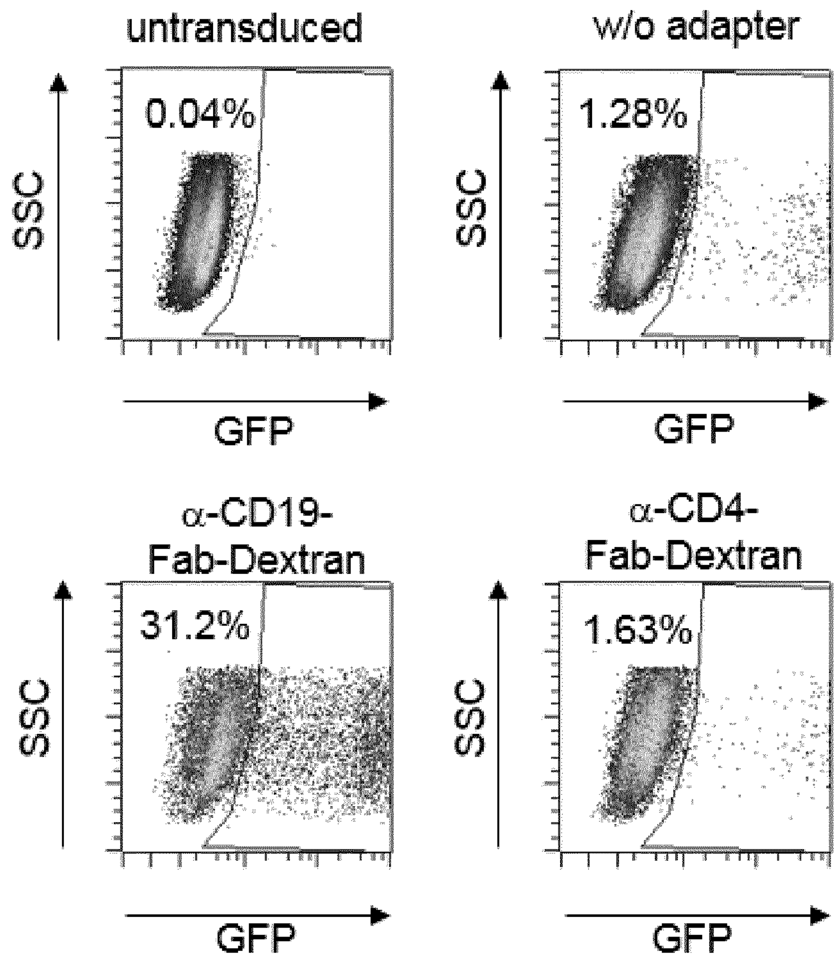

FIG. 12: Evaluation of an alternative adapter format: dextran as tag of a tagged polypeptide. The tagged polypeptide was an Fab fragment coupled to dextran and the tag is dextran. A scFV specific for dextran was fused to Hmut used for pseudotyping.

CD19 positive Raji cells were transduced with GFP encoding α-tag-LV with Vectofusin-1® in the absence (w/o adapter) or presence of tagged α-CD19-Fab or tagged α-CD4-Fab. Three days post transduction the transduction efficiency was determined by quantification of GFP positive cells using flow cytometry.

Figure 13:
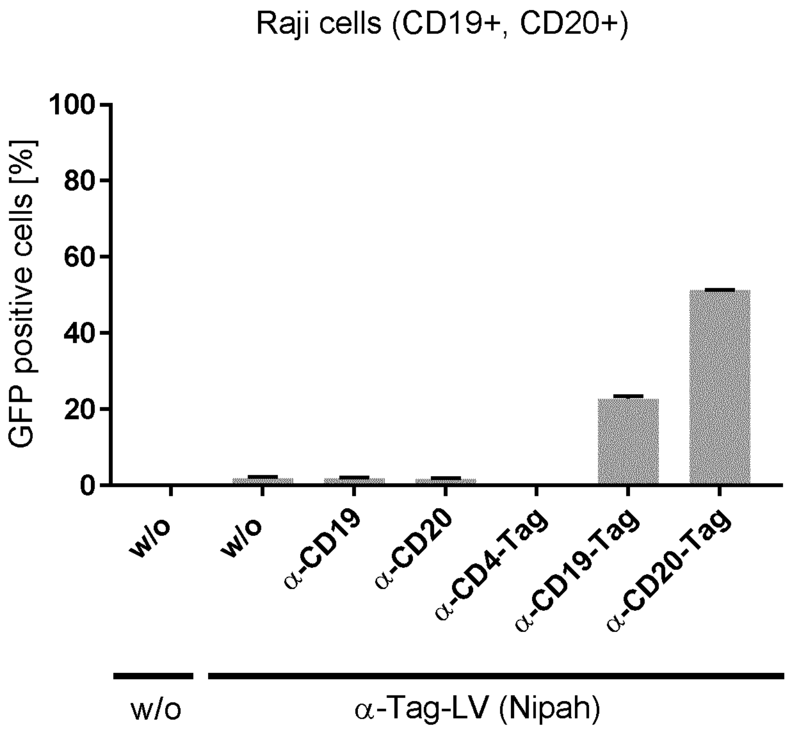

FIG. 13: Adapter-LV using Nipah envelope proteins for pseudotyping: CD19 positive, CD20 positive, CD4 negative Raji cells were incubated in absence (w/o) of any adapter or in presence of the tagged adapter α-CD4-Ab-tag, α-CD19-Ab-tag, α-CD20-Ab-tag, or adapter without any tag α-CD20-Ab or α-CD19-Ab, respectively, for 30 min at 4° C. The tagged polypeptide was a biotinylated antibody and the used tag was biotin. GFP encoding α-tag-LV was applied at a MOI of 0.25. Three days post transduction the transduction efficiency was determined by quantifying GFP positive cells using flow cytometry.

Figure 14:
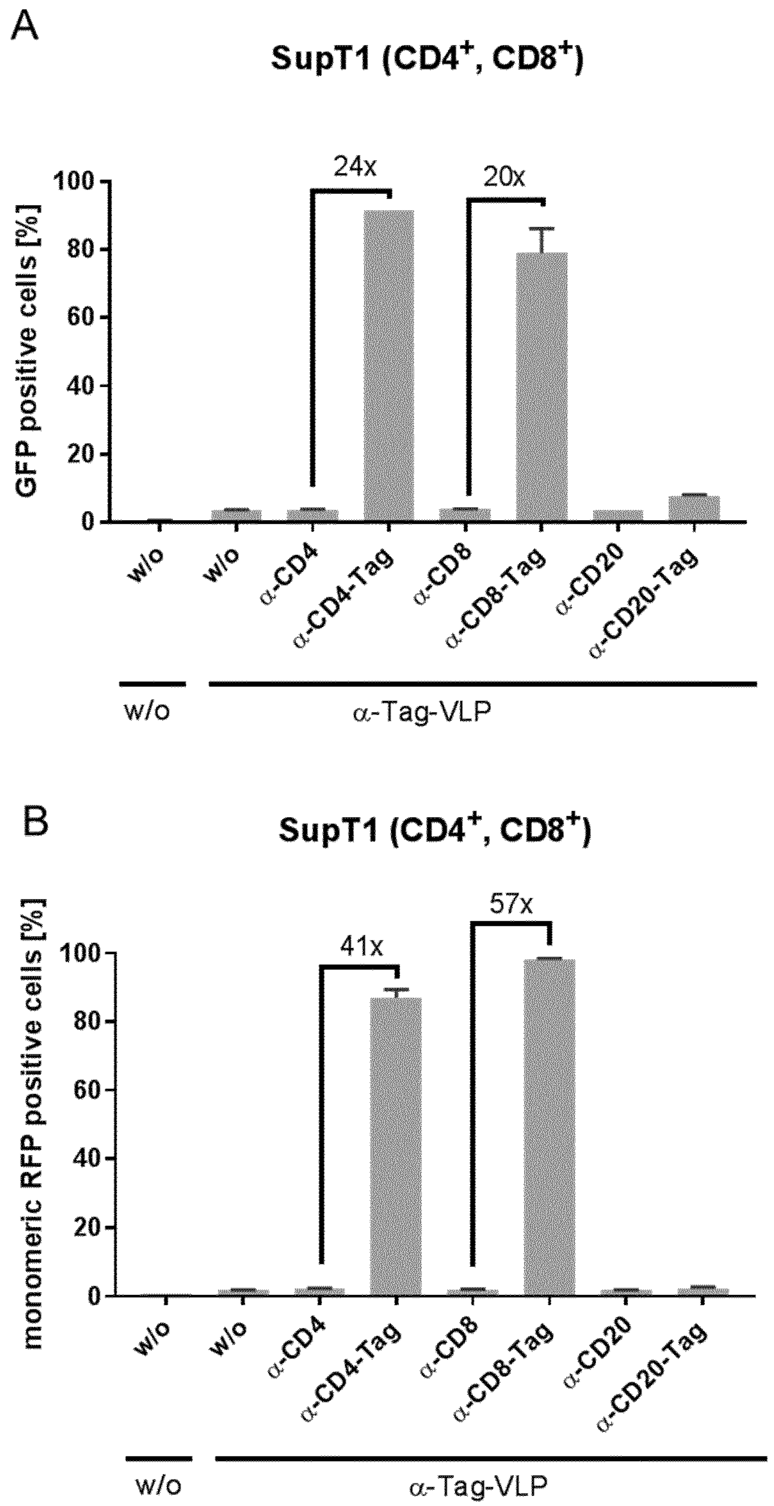

FIG. 14: Adapter-VLP mediated protein transfer: CD4 positive, CD8 positive, CD20 negative SupT1 cells were incubated in absence of any polypeptide (w/o) or in presence of the tagged or untagged polypeptide α-CD4, α-CD8 or α-CD20, respectively, for 30 min at 4° C. The tagged polypeptide was a biotinylated antibody and the used tag comprised biotin. α-tag VLPs without integrating viral genome carrying GFP or monomeric red fluorescent protein were applied at a MOI of 0.05. Four hours post VLP addition the protein transfer efficiency was determined by quantifying GFP or monomeric red fluorescent protein positive cells using flow cytometry.

DETAILED DESCRIPTION OF THE INVENTION

The present invention provides an adaptable transduction system (a composition or formulation) for retroviral vector particles or virus-like particles thereof for targeting different and varying antigens on target cells in the presence of both the retroviral vector or virus-like particle thereof that can bind to a tag and the corresponding tagged polypeptide that can bind to an antigen expressed on a target cell.

In a first aspect the present invention provides a composition comprising i) a pseudotyped retroviral vector particle or virus-like particle thereof comprising:

a) one envelope protein with antigen-binding activity, wherein said envelope protein is a recombinant protein that does not interact with at least one of its native receptors and is fused at its ectodomain to a polypeptide comprising an antigen binding domain specific for a tag of a tagged polypeptide, and wherein said envelope protein is protein G, HN or H derived from the Paramyxoviridae family b) one envelope protein with fusion activity derived from the Paramyxoviridae family, and ii) said tagged polypeptide, wherein said tagged polypeptide binds specifically to an antigen expressed on the surface of a target cell, thereby transducing the target cell with said retroviral vector particle or thereby inducing uptake of the virus-like particle into the target cell.

Said pseudotyped retroviral vectors or virus-like particles thereof may be fused via a linker to the ectodomain of said recombinant protein that does not interact with at least one of its native receptors.

In a preferred embodiment of the invention, the interaction to all native receptors of said recombinant protein is inhibited, then the present invention provides a combination of i) a pseudotyped retroviral vector particle or virus-like particle thereof comprising:

a) one envelope protein with antigen-binding activity, wherein said envelope protein is a recombinant protein that does not interact with its native receptor(s) and is fused at its ectodomain to a polypeptide comprising an antigen binding domain specific for a tag of a tagged polypeptide, and wherein said envelope protein is protein G, HN or H derived from the Paramyxoviridae family b) one envelope protein with fusion activity derived from the Paramyxoviridae family, and ii) said polypeptide, wherein said tagged polypeptide binds specifically to an antigen expressed on the surface of a target cell, thereby transducing the target cell with said retroviral vector particle or thereby inducing uptake of the virus-like particle into the target cell.

In another embodiment of the present invention the interaction to the receptor(s) mainly used for cell entry is inhibited. In another embodiment of the present invention the interaction to at least one receptor is inhibited.

In addition, antibody fragments like scFVs may require linker sequences to fuse both chains of said scFV. The generation of recombinant proteins containing domains or fragments that have been fused to other domains using linker polypeptides is well described in the art (e.g. Chen et al. (2013)). The prototype linker is the (G4S)3 linker that is also used exemplary in the present invention, but no restriction to this prototype linker is intended as other linker sequences may be functional in the context of the present invention as well.

Said tag of said tagged polypeptide is not expressed on any cell of any species (target cells and non-target cells) of a subject or of a cell culture in which said retroviral vector or virus-like particle thereof is applied for transduction, e.g. in a human. As a consequence, said retroviral vector or virus-like particle thereof only may transduce any target cell in the presence of said tagged polypeptide. The non-target cells furthermore are not transduced in the presence of said tagged polypeptide.

Said pseudotyped retroviral vector particle or virus-like particle thereof, wherein said envelope protein with antigen-binding activity does not bind to any antigen of the target cell without said tagged polypeptide.

Said pseudotyped retroviral vector particle or virus-like particle thereof, wherein said transduction or said induced uptake may be at least 2-fold higher, 5-fold-higher, 10-fold higher, 25-fold higher, 50-fold higher, 100-fold higher, 1000-fold higher, 2000-fold-higher or 5000-fold higher on said target cells in the presence of said tagged polypeptide compared to said transduction or said induced uptake on said target cells in the absence of said tagged polypeptide. Said pseudotyped retroviral vector particle or virus-like particle thereof, wherein said envelope protein with antigen-binding activity does not bind to any target and non-target-cell without said tagged polypeptide.

Said pseudotyped retroviral vector particle or virus-like particle thereof, wherein no human cell is transduced without said tagged polypeptide.

Said pseudotyped retroviral vector particle or virus-like particle thereof, wherein generation, use and administration of said pseudotyped retroviral vector particle or virus-like particle thereof may be performed in lower risk environment as no human cell is transduced without said tagged polypeptide.

Said pseudotyped retroviral vector particle or virus-like particle thereof, wherein no cell of any species (target cells and non-target cells) may be transduced without said tagged polypeptide.

Said pseudotyped retroviral vector particle or virus-like particle thereof, wherein the antigen that is bound by said tagged polypeptide is expressed transiently.

Said pseudotyped retroviral vector particle or virus-like particle thereof, wherein the antigen that is bound by said tagged polypeptide may be expressed transiently, depending on the cell cycle phase or the state of activation and/or differentiation.

Said pseudotyped retroviral vector particle or virus-like particle thereof, wherein the expression of the antigen that is bound by said tagged polypeptide may be controllable, e.g. by inducible expression.

Said pseudotyped retroviral vector particle or virus-like particle thereof, wherein said transduction or said induced uptake may be at least 2-fold higher, 5-fold-higher, 10-fold higher, 25-fold higher, 50-fold higher, 100-fold higher, 1000-fold higher, 2000-fold-higher or 5000-fold higher on said target cells than on non-target cells.

Said pseudotyped retroviral vector particle or virus-like particle thereof, wherein said Paramyxoviridae virus may be a virus of the morbillivirus genus or of the *Henipavirus* genus.

Pseudotyping retroviral vectors with Paramyxoviridae derived envelope proteins is well described in the art. For efficient pseudotyping of retroviral vectors with envelope proteins derived from the genus morbillivirus the truncated cytoplasmic portion of the F protein should comprise at least 1 positively charged amino acid residue and no more than 9 consecutive amino acid residues as counted from the N-terminal end of the cytoplasmic portion of the F protein and the truncated cytoplasmic portion of the H protein should comprise at least 9 and no more than 19 consecutive amino acid residues as counted from the C-terminal end of the cytoplasmic portion of the H protein plus an additional methionine at the N-terminus (Frecha et al. (2008), EP2066795B9, Edes (2016)). Thus, lentiviral vectors and gammaretroviral vectors are efficiently pseudotyped using truncated F and H protein variants as described above.

Several reports show that retroviral vectors can also be pseudotyped with envelope proteins from Nipah virus. It is a virus derived from the family Paramyxoviridae, subfamiliy Paramyxovirinae, genus *Henipavirus*. Another member of this genus is Hendravirus. In contrast to the H protein of morbillivirus, the Nipah envelope protein with antigen-binding function is the G protein. It has no hemagglutinating function but it is also TypeII membrane protein.

Although the cytoplasmic domain of the G protein is quite long and thus potentially requires larger deletions within the cytoplasmic domain for efficient pseudotyping, several reports show data of different truncations and functional titers even without any truncation within the cytoplasmic domain of the G protein (Khetawat et al. (2010), Bender et al. (2016) Palomares et al. (2013)). For the Nipah F protein a similar observation has been made indicating that for both virus envelope proteins truncations of the cytoplasmic domains are less critical to yield functional retroviral vectors titers. However, Bender et al. (2016) have shown that the highest retroviral vector titer was detected when constructs with remaining 11 amino acids plus methionine at the cytoplasmic domain of the G protein and 6 remaining acids at the cytoplasmic domain of the F protein were used. In contrast, Khetawat et al. (2010) have observed the highest retroviral vector titer with the untruncated version of the G protein and 4 remaining acids on the cytoplasmic domain of the F protein. The results of Palomares et al. (2013) indicate that the untruncated version or the version with 35 or 20 remaining amino acids plus methionine at the cytoplasmic domain of the G protein in combination with 6 remaining amino acids plus 6 additional amino acids of the Nipah F protein resulted in highest retroviral vector titers.

In addition, lentiviral vectors were successfully pseudotyped with envelope proteins derived from another virus within the Paramyxoviridae family: Tupaia virus (Enkrich et al. (2013)). It is related to morbillivirus and *Henipavirus* but not assigned to one of these genera because it is genetically too different. Albeit the genetic difference is too high, a comparable truncation of the cytoplasmic domain as for the morbillivirus envelope proteins is necessary to enable pseudotyping at high efficiency: 6 remaining amino acids of the cytoplasmic domain of the F protein and 13 remaining amino acids plus methionine at the cytoplasmic domain of the H protein resulted in the highest retroviral vector titer.

Said pseudotyped retroviral vector particle or virus-like particle thereof, wherein said protein derived from protein G, H, HN or F of a virus of the Paramyxoviridae family lacks at least one part of the cytoplasmic region of said protein G, H, HN or F, i.e. said protein G, H, HN or F may be a truncated protein.

Said pseudotyped retroviral vector particle or virus-like particle thereof, wherein said protein derived from protein G, H, or F of a virus of the genus morbillivirus or *Henipavirus* lacks at least one part of the cytoplasmic region of said protein G, H, or F, i.e. said protein G, H, HN or F may be a truncated protein.

Said pseudotyped retroviral vector particle or virus-like particle thereof, wherein said protein derived from protein H or F of a virus of the genus morbillivirus lacks at least one part of the cytoplasmic region of said protein H, or F, i.e. said protein H or F may be a truncated protein.

Said pseudotyped retroviral vector particle or virus-like particle thereof, wherein said protein derived from protein G or F of a virus of the genus *Henipavirus* lacks at least one part of the cytoplasmic region of said protein G or F, i.e. said protein G or F may be a truncated protein.

Said pseudotyped retroviral vector particle or virus-like particle thereof, wherein said protein derived from protein H or F of the measles virus lacks at least one part of the cytoplasmic region of said protein H or F, i.e. said protein H or F may be a truncated protein.

Said pseudotyped retroviral vector particle or virus-like particle thereof, wherein said protein derived from protein G or F of the Nipah virus lacks at least one part of the cytoplasmic region of said protein G or F, i.e. said protein G or F may be a truncated protein.

Said pseudotyped retroviral vector particle or virus-like particle thereof, wherein said envelope protein with fusion activity derived from the Paramyxoviridae family lacks at least one part of the cytoplasmic region of said envelope protein.

Said pseudotyped retroviral vector particle or virus-like particle thereof, wherein said morbillivirus is a measles virus or the Edmonston strain of measles virus.

Said retroviral vector particle or virus-like particle thereof, wherein said *Henipavirus* is a Nipah virus.

Said retroviral vector particle or virus-like particle thereof, wherein said truncated Paramyxoviridae virus envelope proteins are a fusion (F) protein with fusion activity and an attachment (G) protein with antigen-binding activity of a *Henipavirus.*

Said pseudotyped retroviral vector particle or virus-like particle thereof, wherein said retroviral vector particle is a lentiviral or gammaretroviral vector particle or a virus particle thereof.

Said retroviral vector particle or virus-like particle thereof, wherein the pseudotyped retroviral vector particle or virus-like particle thereof is derived from a lentivirus selected from the group consisting of HIV-1, HIV-2, SIVmac, SIVpbj, SIVagm, FIV and EIAV.

Said retroviral vector particle or virus-like particle thereof, wherein the pseudotyped retroviral vector particle or virus-like particle thereof is derived from a gammaretrovirus selected from the group consisting of feline leukemia virus, Gibbon ape leukemia virus (GALV) and murine leukemia virus (MLV).

Said retroviral vector particle or virus-like particle thereof, wherein the cytoplasmic portions of said F and H proteins are truncated by deletion of amino acid residues from said cytoplasmic portions, and wherein the truncated cytoplasmic portion of the F protein comprises at least 1 positively charged amino acid residue and no more than 9 consecutive amino acid residues as counted from the N-terminal end of the cytoplasmic portion of the F protein, wherein the truncated cytoplasmic portion of the H protein comprises at least 9 and no more than 19 consecutive amino acid residues as counted from the C-terminal end of the cytoplasmic portion of the H protein plus an additional methionine at the N-terminus.

Said truncated cytoplasmic portion of the H protein is truncated to allow efficient pseudotyping and has fusion support function.

Said retroviral vector particle or virus-like particle thereof, wherein said particle comprises a fusion (F) and a hemagglutinin (H) protein of a morbillivirus, wherein the cytoplasmic portions of said F and H proteins are truncated by deletion of amino acid residues from said cytoplasmic portions and wherein the truncated cytoplasmic portion of the F protein comprises at least 1 positively charged amino acid residue and no more than 9 consecutive amino acid residues as counted from the N-terminal end of the cytoplasmic portion of the F protein, the truncated cytoplasmic portion of the H protein is truncated to allow efficient pseudotyping and has fusion support function, wherein the truncated cytoplasmic portion of the H protein comprises at least 9 and no more than 19 consecutive amino acid residues as counted from the C-terminal end of the cytoplasmic portion of the H protein plus an additional methionine at the N-terminus, and wherein the truncated H protein is a chimeric protein that does not interact with CD46, SLAM and further has at its ectodomain a polypeptide comprising an antigen binding domain specific for a tag of a tagged polypeptide, and wherein said tagged polypeptide binds specifically to an antigen expressed on the surface of a target cell.

Said retroviral vector particle or virus-like particle thereof, wherein said particle comprises a fusion (F) and a hemagglutinin (H) protein of the measles virus or the Edmonston strain of measles virus, and/or wherein the truncated cytoplasmic portion of the F protein comprises at least 3 consecutive amino acid residues as counted from the N-terminal end of the cytoplasmic portion of the F protein and the truncated cytoplasmic portion of the H protein comprises at least 13 consecutive amino acid residues as counted from the C-terminal end of the cytoplasmic portion of the H protein plus an additional methionine at the N-terminus, wherein one to four of the N-terminal amino acid residues of said at least 13 consecutive amino acid residues as counted from the C-terminal end of the cytoplasmic portion of the H protein can be replaced by alanine residues, and/or wherein the pseudotyped retroviral vector particle or virus-like particle thereof is derived from a lentivirus selected from the group consisting of HIV-1, HIV-2, SIVmac, SIVpbj, SIVagm, FIV and EIAV, and/or wherein the truncated F protein is FcA24 or FcΔ30 and/or the truncated H protein is selected from the group consisting of Hc14, Hc15, HcΔ16, HcΔ17, HcΔ18, HcΔ19, HcΔ20, HcΔ21+A and HcΔ24+4A.

Said composition of retroviral vector particle or virus-like particle and tagged polypeptide, wherein the polypeptide of said tagged polypeptide may be a protein with antigen binding moieties to the antigen expressed on the target cell such as an antibody or antigen binding fragment thereof, cytokines or growth factors.

Said polypeptide of said tagged polypeptide may be an antibody or antigen binding fragment thereof, wherein said antibody or antigen binding fragment thereof binds to said antigen expressed on the surface of said target cell, and wherein the tag of said tagged polypeptide may be a hapten.

Said hapten may be selected from the group consisting of biotin, fluorescein isocyanate (FITC), fluorescein, NHS-fluorescein, 2,4-dinitrophenol (DNP), digoxigenin and dextran.

Said hapten may be biotin.

Said polypeptide of said tagged polypeptide may bind to an antigen expressed on the surface of said target cell, and wherein binding of said polypeptide to said antigen may activate said target cell.

Said tag may be catalytically degradable.

Said polypeptide comprising an antigen binding domain specific for a tag of a tagged polypeptide, and wherein said antigen binding domain is derived of a scFV derived from an antibody and wherein the amino acid sequence has been mutated in the framework region of said scFV to improve surface expression and/or stability of said polypeptide.

Said polypeptide of said tagged polypeptide may be an antigen binding moiety (ABM), wherein the tag of said tagged polypeptide is a linker/label epitope (LLE) of a target cell binding molecule (TCBM) comprising i) an antigen binding moiety (ABM), wherein said ABM binds specifically to said antigen expressed on the surface of said target cell, ii) a label moiety (LaM), wherein said LaM is a naturally occurring molecule in a subject or a derivative thereof, iii) a linker moiety (LiM) conjugating said ABM and said LaM, thereby forming a linker/label epitope (LLE), wherein said antigen binding domain of said polypeptide specific for a tag is linker/label epitope (LLE) binding domain, wherein said LLE binding domain binds said LLE with a higher preference than said naturally occurring molecule.

Said LLE binding domain may bind with an at least twofold, preferentially at least 5-fold, more preferentially at last 10-fold, most preferentially at least 50-fold higher affinity to said LLE than to said naturally occurring molecule.

The k(off) value for the binding between said LLE binding domain may be higher to a monomeric LLE and said naturally occurring molecule than to a multimeric LLE.

Said naturally occurring molecule may be in the circulatory system of said subject.

Said LLE may be generated site-specifically, thereby forming an epitope comprising a part of said LaM and a part of said LiM.

Said LaM may be selected from the group consisting of amino acids, peptides, proteins, creatinine, biotin, biocytin, lipids, hormones, vitamins, carbohydrates or a derivative thereof.

Said LiM may be a molecule capable of generating said LLE.

Said LiM may be selected from the group consisting of peptides, proteins, nucleic acids, carbohydrates, polyhydroxyalkanoates, alkyl chains, alkanoic acids, carboxylic acids, farnesyls, polyethylene glycols, lipids or a derivative thereof.

Said LaM may be biotin or a derivative thereof and said LiM may be a 6-(6-aminohexanamido) hexanoyl moiety or a 6-aminohexanoyl moiety.

Said LLE binding domain may comprise the sequence of SEQ ID NO: 1 and SEQ ID NO: 2, preferentially the order of the sequence from N-terminus to C-terminus is VH-VL.

Said antigen of said tagged polypeptide may be selected from the group consisting of TCR, CD3, CD4, CD8, CD25, CD62L, CD69, CD137, CD44, CD45RA, CD45RO, CD137, CD152, CD154, CCR5, CCR7, PD-1, CTLA-4, CD105, NKR-PiA, CD56, NCAM-1, CD57, CD14, CD16, CD19, CD20, CD30, CD34, CD133, CD38, BDCA-1, BDCA-2, BDCA-3, GM-CSF, CD11b, A2B5, ACSA-2, GLAST, AN2, CX3CR1, O4, CD15, CD11, CD144, SSEA-4, TRA-1 CD33 (Siglec-3), CD123 (IL3RA), CD135 (FLT-3), CD44 (HCAM), CD44V6, CD47, CD184 (CXCR4), CLEC12A (CLL1), LeY, FRβ, MICA/B, CD305 (LAIR-1), CD366 (TIM-3), CD96 (TACTILE), CD29 (ITGB1), CD47 (IAP), CD66 (CEA), CD112 (Nectin2), CD117 (c-Kit), CD146 (MCAM), CD155 (PVR), CD171 (L1CAM), CD221 (IGF1), CD227 (MUC1), CD243 (MRD1), CD246 (ALK), CD271 (LNGFR), GD2, and EGFR.

Said ABM may be an antibody or an antigen-binding fragment thereof.

Said target cell may be selected from the group consisting of immune cells, hematopoietic cells, stem cells, muscle cells, cancerous cells, cells of the nervous system, endothelial progenitor cells (EPCs), endothelial cells and diseased cells.

Any of the above disclosed variants and embodiments of the combination of retroviral vector particles or virus-like particles thereof and tagged polypetides may be combined with each other.

In a second aspect the present invention provides a pseudotyped retroviral vector particle or virus-like particle thereof comprising:

a) one envelope protein with antigen-binding activity, wherein said envelope protein is a recombinant protein that does not interact with at least one of its native receptor(s) and is fused at its ectodomain to a polypeptide comprising an antigen binding domain specific for a tag of a tagged polypeptide, and wherein said envelope protein is protein G, HN or H derived from the Paramyxoviridae family b) one envelope protein with fusion activity derived from the Paramyxoviridae family; and wherein said tagged polypeptide binds specifically to an antigen expressed on the surface of a target cell, thereby transducing the target cell with said retroviral vector particle or thereby inducing uptake of the virus-like particle into the target cell.

In a third aspect the present invention provides a pharmaceutical composition comprising the pseudotyped retroviral vector particle or virus-like particle thereof as disclosed herein and the tagged polypeptide as disclosed herein, optionally further comprising a pharmaceutically acceptable carrier.

In a fourth aspect the present invention provides a composition of the pseudotyped retroviral vector particle or virus-like particle thereof and the tagged polypeptide as disclosed herein for use as a medicament.

In a fifth aspect the present invention provides the use of the composition of the pseudotyped retroviral vector particle or virus-like particle thereof and the tagged polypeptide as disclosed herein for the preparation of a medicament.

In a sixth aspect the present invention provides a method for producing a pseudotyped retroviral vector particle or virus-like particle thereof, the method comprising:

co-transfecting of a packaging cell line with at least one psi-negative expression vector encoding retroviral gag/pot/rev genes, a psi-positive retroviral expression vector and one or two psi-negative expression vector(s) encoding for Paramyxoviridae virus envelope proteins as disclosed herein.

In a seventh aspect, the present invention provides an in vitro method for transducing target cells with a pseudotyped retroviral vector particle or delivery of the proteins of the virus-like particle thereof as disclosed herein comprising the steps a) preincubation of target cells with a tagged polypeptide as disclosed herein, and b) addition of said retroviral vector particle or vector-like particles thereof to the preincubated target cells of step a).

Surprisingly, it was found that the order of adding tagged polypeptide, target cells and retroviral vector of the method as disclosed herein strongly influences the transduction efficacy (see FIG. 5).

Said method, wherein in step b) additionally a transduction enhancer may be used.

Said method, wherein said enhancer may be the LAH4 peptide having the sequence represented in SEQ ID NO: 15 ("Vectofusin-1®) or a functional derivative thereof having the ability to improve the transduction efficiency or the uptake of a retroviral vector or virus-like particle into the target cell.

In an eighth aspect, the present invention provides an in-vivo method for transducing a hematopoietic cell, preferably an immune subset cell or a stem cell, comprising Administering a formulation of tagged polypeptides as disclosed herein to subject in need of treatment, wherein said tagged polypeptides bind a target cell, wherein said target cell is a hematopoietic cell, preferentially immune subset cell such as a T cell or NK cell, NKT cell, B cell, macrophage, dendritic cell, or a stem cell capable of giving rise to said immune subset cell, Administering a formulation of pseudotyped retrovirus vector particles or virus-like particles thereof as disclosed herein to the subject, wherein said pseudotyped retrovirus vector particles or virus-like particles thereof bind the tagged polypeptides, thereby transducing the target cell with said retroviral vector particle or thereby inducing uptake of the virus-like particle into the target cell Said method, wherein said pseudotyped retrovirus vector particles or virus-like particles carry at least one transgene thereby transducing said transgene into the target cell, and thereby enabling immunotherapy of the subject by the transduced cells after expression of said transgene in the target cells.

Said method, wherein said transgene is a gene encoding for instance for a chimeric antigen receptor.

In a ninth aspect, the present invention provides an in-vivo method for transducing a defective stem cell, comprising a) Administering a formulation of tagged polypeptides as disclosed herein to subject in need of treatment, wherein said tagged polypeptides bind a target cell, wherein said target cell is a defective stem cell b) Administering a formulation of pseudotyped retrovirus vector particles or virus-like particles thereof as disclosed herein to the subject, wherein said pseudotyped retrovirus vector particles or virus-like particles thereof bind the tagged polypeptides, thereby transducing the target cell with said retroviral vector particle or thereby inducing uptake of the virus-like particle into the target cell.

Said method, wherein said pseudotyped retrovirus vector particles or virus-like particles carry at least one transgene thereby transducing said transgene into the target cell.

Said method, wherein said transgene encodes for a non-mutated allele of a monogenic disease such as Beta-thalassemia, SCID-X1, Wiskott-Aldrich syndrome, thereby correcting the defective stem cell to be a non-defective stem cell.

In a variant of the retroviral vector particle or virus-like particle thereof as disclosed herein, the envelope protein with antigen-binding activity, wherein said envelope protein is a recombinant protein that does not interact with at least one of its native receptors and is not fused to the polypeptide comprising an antigen binding domain specific for a tag of a tagged polypeptide, and wherein said envelope protein is protein G, HN or H derived from the Paramyxoviridae family. In this variant, said polypeptide comprising an antigen binding domain specific for a tag of a tagged polypeptide is fused to another membrane protein or a fragment thereof present in the envelope of the retrovirus vector particle or the virus-like particle thereof, resulting in three discrete proteins anchored in the envelope. Therefore, in this variant the pseudotyped retroviral vector particle or the virus-like particle thereof comprises a) one envelope protein with antigen-binding activity, wherein said envelope protein is a recombinant protein that does not interact with at least one of its native receptors, wherein said envelope protein is protein G, HN or H derived from the Paramyxoviridae family b) one envelope protein with fusion activity derived from the Paramyxoviridae family; and c) one membrane protein or a fragment thereof comprising an antigen binding domain specific for a tag of a tagged polypeptide, wherein said tagged polypeptide binds specifically to an antigen expressed on the surface of a target cell, thereby transducing the target cell with said retroviral vector particle or thereby inducing selective uptake of the virus-like particle (VLP) into the target cell.

All definitions, characteristics and embodiments defined herein with regard to the first aspect of the invention, the composition comprising the pseudotyped retroviral vector particle or virus-like particle thereof as disclosed herein and the tagged polypeptide as disclosed herein, also apply mutatis mutandis in the context of the other aspects of the invention as disclosed herein.

Embodiments

In addition to above described applications of the adaptable retroviral vector particle system as disclosed herein or the virus-like particle system as disclosed herein, further embodiments of the invention are described in the following without intention to be limited to these embodiments.

In a preferred embodiment of the adaptable retroviral vector system target cells present in a mixed cell population with non-target cells are selectively transduced or VLP uptake is selectively induced.

In another embodiment of the adaptable retroviral vector system the specificity of the tagged polypeptide is adjusted according to the expression level of an antigen on the target cells.

For example, cells or cell types that do not express sufficient levels of VSV-G receptors and therefore are resistant to VSV-G pseudotyped retroviral vector transduction may be more efficiently transduced using the adaptable retroviral vector system and tagged polypeptides specific for antigens of receptors that are expressed at higher levels as compared to the expression levels of the VSV-G receptor.

In another embodiment of the adaptable retroviral vector system, activation of the target cells is induced upon binding of the retroviral vector particle or virus-like particle complex to the target antigen.

In another embodiment of the adaptable retroviral vector system target cell populations expressing different antigens may be simultaneously or subsequently transduced by combining tagged polypeptides with different specificities.

In another embodiment of the adaptable retroviral vector system target cells that are characterized by multiple antigens are selectively transduced or have taken up VLPs selectively if tagged polypeptides specific for all antigens are required to induce selective transduction or VLP uptake.

In another embodiment of the adaptable retroviral vector system the transduction efficiency or VLP uptake is reduced by releasing the retroviral vector from the tagged polypeptide by adding an alternative polypeptide or ligand, wherein said alternative polypeptide or ligand binds with preferably higher affinity to a tag on a tagged adapter as compared to the polypeptide specific for the tag that is fused to the ectodomain of said envelope protein of said retroviral vector or virus-like particle thereof.

For example: the addition of avidin, a ligand of biotin, to tag-specific retroviral vector bound to tagged polypeptide may reduce or inhibit this binding and the transduction or VLP uptake is reduced.

In another embodiment of the adaptable retroviral vector system the transduction efficiency or VLP uptake is reduced by removing or degrading said tag of said tagged polypeptide.

In another embodiment of the adaptable retroviral vector system the transduction efficiency or VLP uptake is reduced by removing or degrading said tagged polypeptide.

In another embodiment of the adaptable retroviral vector system the transduction efficiency or VLP uptake is reduced by adding an alternative tag, wherein said retroviral vector or virus-particle thereof binds preferably with higher affinity to the alternative tag and the retroviral vector or virus-like particle thereof does not bind to the tagged polypeptide anymore.

In another embodiment of the adaptable retroviral vector system the transduction efficiency or VLP uptake is reduced by adding tag molecules in excess, wherein said retroviral vector or virus-particle thereof preferentially binds added tag.

In another embodiment of the adaptable retroviral vector system the transduction efficiency or VLP uptake is reduced by adding an alternative tagged polypeptide, wherein said alternative adapter is specific for the same antigen but binds with higher affinity to said antigen expressed on said target cell.

In another embodiment of the adaptable retroviral vector system the transduction efficiency or VLP uptake is reduced by removing or degrading said polypeptide that is fused to the ectodomain of said envelope protein with antigen-binding activity.

In another embodiment of the adaptable retroviral vector system the transduction efficiency or VLP uptake is controlled by modifying the affinity and/or avidity of said tagged polypeptide to said antigen expressed on said target cell.

In another embodiment of the adaptable retroviral vector system the transduction efficiency or VLP uptake is controlled by varying the amount of said tagged polypeptide.

In another embodiment of the adaptable retroviral vector system the selective transduction or VLP uptake takes place in vivo.

In another embodiment of the adaptable retroviral vector system the selective transduction or VLP uptake takes place in vitro or in vivo and is used to screen and identify antigens that are bound by said tagged polypeptide.

In another embodiment of the adaptable retroviral vector system the selective transduction or VLP uptake takes place in vitro or in vivo and is used to screen and identify antigens and/or target cells that are bound by said tagged polypeptide.

In another embodiment of the adaptable retroviral vector system the selective transduction or VLP uptake takes place in vitro or in vivo and is used to screen and identify polypeptides that bind to target antigens expressed on target cells.

In another embodiment of the adaptable retroviral vector system the retroviral vector or VLP thereof delivers a gene of interest to generate a recombinant cell or animal.

In another embodiment of the adaptable retroviral vector system the retroviral vector or VLP thereof delivers a gene of interest encoding a therapeutic protein to treat or prevent disease.

In another embodiment of the adaptable retroviral vector system the retroviral vector or VLP thereof delivers a protein of interest that may be used for vaccination purposes or gene editing with, for example, Crispr/Cas.

In another embodiment of the adaptable retroviral vector system the retroviral vector is integration-deficient.

Definitions

Unless defined otherwise, technical and scientific terms used herein have the same meaning as commonly understood by one of ordinary skill in the art to which this invention belongs.

Retroviridae is virus family with a single-stranded, diploid, positive-sense RNA genome that is reverse-transcribed into a DNA intermediate that is then incorporated into the host cell genome. Retroviridae-derived viruses are enveloped particles with a diameter of 80-120 nm. (Retro-/lenti-/gammaretro-) viral vectors are replication-deficient viral particles that are derived from the corresponding virus family. They contain Gag and Pol proteins, a single-stranded RNA genome and are usually pseudotyped with heterologous envelope proteins derived from other viruses. The RNA genome of said viral vectors do not contain any viral gene to produce viral progeny, but psi elements and LTRs that are required for efficient packing and reverse transcription in DNA. The DNA intermediate may contain a gene of interest under the control of a suitable promoter, for example, the CMV promoter and the gene of interest is expressed upon integration of said DNA into the genome of the host cell. The process of entering the host cell, delivering the RNA genome, integration and expression of the gene of interest is called transduction. The minimal requirements of a gammaretrovirus or lentivirus based viral vector has been well-described in the art.

In addition, integrase-deficient retroviral vectors (ID-RVs) have been developed that cannot integrate the retroviral vector genome in the host cell genome. ID-RVs are derived from conventional retroviral vectors but contain no or a mutated form of the retroviral integrase. Upon entry into the host cell, the retroviral vector genome is reverse-transcribed in the cytoplasm, delivered into the nucleus, but not stably integrated into the host cell genome. ID-RVs are useful tools to express the gene of interest transiently. The definition of retroviral vectors and transduction also extents the integration-deficient retroviral vectors and its application.

Lentivirus is a genus of Retroviridae that cause chronic and deadly diseases characterized by long incubation periods, in the human and other mammalian species. The best-known lentivirus is the Human Immunodeficiency Virus HIV which can efficiently infect nondividing cells, so lentiviral derived retroviral vectors are one of the most efficient methods of gene delivery.

Gammaretroviridae is a genus of the Retroviridae family. Representative species are the murine leukemia virus and the feline leukemia virus.

Paramyxoviridae is a family of viruses in the order of Mononegavirales. There are currently 49 species in this family, divided among 7 genera. Diseases associated with this virus family include measles, mumps, and respiratory tract infections. Members of this virus family are enveloped viruses with a non-segmented, negative-strand RNA genome of about 16 kb. Two membrane proteins with two distinct functions appear as spikes on the virion surface. The H/HN/G proteins mediate binding to the receptor at the cell surface.

Thus, the term “virus envelope protein(s) that have antigen binding activity” as used herein refers to protein(s) on the viral envelope that are responsible for binding to complementary receptors or antigens on the cell membrane of a target cell. For Paramyxoviridae H, HN or G proteins are virus envelope protein(s) that have antigen binding activity.

Upon binding the H/HN/G proteins change their conformation that induces a process called fusion helper function, leading to subsequent conformational changes within the F protein that is mediating the fusion of the viral and cellular membrane. The capsid and viral genome may now enter and infect or transduce the host cell. The term “virus envelope proteins(s) that have fusion activity” as used herein refers to protein(s) that initiate fusion of viral and cellular membrane. For Paramyxoviridae F proteins refer to virus envelope protein(s) that have fusion activity.

Virus-like particles (VLPs) resemble viral particles, but are not infecting or transducing because they contain no viral genetic material encoding for the proteins of the virus-like particle. In particular, VLPs in the context of retroviral vectors do not contain psi positive nucleic acid molecules. Some virus-like particles may contain nucleic acid distinct from their genome. The expression of viral structural proteins, such as envelope or capsid, can result in the assembly of virus like particles (VLPs). Like for retroviral vectors VLPs can also be pseudotyped using the same envelope constructs as for retroviral vectors. VLPs may be used to deliver proteins but also nucleic acids to the cytoplasm of target cells. In particular, VLPs are useful as vaccines. The term “VLP uptake” as used herein refers to the binding of a VLP to the target cell membrane, thereby releasing nucleic acid molecules, proteins or peptides into the target cell. Chimeric proteins are proteins created through the joining of two or more genes that originally coded for separate proteins. Translation of this gene results in a single or multiple polypeptides with functional properties derived from each of the original proteins. Recombinant proteins are created artificially by recombinant DNA technology for use in biological research or therapeutics.

The term “ectodomain” as used herein refers to a domain of a membrane protein that extends into the extracellular space (the space outside a cell).

The term "activation" as used herein refers to inducing physiological changes with a cell that increase target cell function, proliferation and/or differentiation.

The term "pseudotyping" or "pseudotyped" as used herein refers to a vector particle bearing envelope glycoproteins derived from other viruses having envelopes. The host range of the lentiviral vectors or vector particles of the present invention can thus be expanded or altered depending on the type of cell surface receptor used by the glycoprotein.

To generate retroviral vectors the gag, pol and env proteins needed to assemble the vector particle are provided in trans by means of a packaging cell line, for example, HEK-293T. This is usually accomplished by transfection of the packaging cell line with one or more plasmids containing the gag, pol and env genes. For the generation of pseudotyped vectors, the env gene, originally derived from the same retrovirus as the gag and pol genes and as the RNA molecule or expression vector, is exchanged for the envelope protein(s) of a different enveloped virus. As an example, the F and H or HN or G protein of Paramyxoviridae is used. Thus, an exemplary pseudotyped vector particle based on the HIV-1 retrovirus comprises the (1) HIV-1 Gag and Pol proteins, (2) an RNA molecule derived from the HIV-1 genome that may be used to generate a retroviral vector particle based on the HIV-1 genome lacking the gag, env, pol, tat, vif, vpr, vpu and nef genes, but still comprising the LTRs, the psi element and a CMV promoter followed by the gene to be transduced, for example, a gene for the GFP protein, and (3) the F and H proteins of measles virus, for example, in a truncated form.

The term "native receptor" as used herein refers to the receptor or antigen expressed on the cell surface of a cell that is bound by the naturally occurring virus envelope protein with antigen (receptor) binding activity. The native measles virus receptors are SLAM, nectin-4 and CD46. Nipah envelope proteins use ephrin-B2 and ephrin-B3 as receptors for entry.

The term "one envelope protein with antigen-binding activity that does not interact with at least one of its native receptor(s)" as used herein means that said protein has reduced or ablated interaction with at least one receptor of a cell that is normally targeted by the virus having said protein as described elsewhere herein. Reduced interaction means that said truncated and/or mutated protein interacts with said at least one native receptor at least 50% less efficient, at least 60% less efficient, at least 70% less efficient, at least 80% less efficient, at least 90% less efficient, at least 95% less efficient, at least 99% less efficient compared to the non-mutated protein. Preferentially said protein does not interact anymore with said at least one of its native receptors. The interaction may be the binding of these two molecules to each other. The less efficient interaction may be a reduced affinity of said protein to its native receptor. Said envelope protein with antigen-binding activity may have more than one native receptors, then the reduction or ablation of interaction of one of these native receptors of said protein results in a reduced tropism of the vector particle or virus-like particle thereof. The more interactions of said protein with its native receptors are inhibited by mutation the more effective is the reduction of tropism of the vector particle or virus-like particle thereof.

In some cases it may be sufficient to inhibit the interaction of some but not all native receptors to said protein as the remaining interactions are not of relevance in the intended application or use of the retroviral vector particle or virus-like particle thereof as disclosed herein, e.g. when a native receptor is not expressed on any cell (target cells and non-target cells) in the environment of target cells that are intended to be transduced.

If an envelope protein with antigen-binding activity has more than 2 native receptors, e.g. 3 native receptors, then preferentially said protein does not interact with the majority of its native receptors, e.g. 2 from 3.

More preferentially, the envelope protein with antigen-binding activity does not interact with all of its native receptors.

The term "tropism" as used herein refers to the host range or specificity of a virus, retroviral vector or virus-like particle thereof. As used herein, the tagged polypeptide specific for antigen expressed on target cells defines the host range of the retroviral vector or virus-like particle thereof.

The term "not human tropic" as used herein refers to the inability of a virus, retroviral vector or virus-like particle thereof to infect, transduce or induce VLP uptake because the virus envelope protein(s) that have antigen binding activity has been mutated to reduce, preferentially ablate binding to any antigen expressed on human cells.

The term "target cell" as used herein refers to a cell which expresses an antigen (a marker) on its cell surface that should be recognized (bound) by the tagged polypeptide of the adaptable system as disclosed herein. The target cell may be a eukaryotic primary cell or a cell line. The target cell may be a mammalian cell such as a murine cell, preferentially the target cell is a human cell.

The term "non-target cells" as used herein refers to a cell which does not express the antigen (a marker) on its cell surface that should be recognized (bound) by the tagged polypeptide of the adaptable system as disclosed herein.

The term "selective" and "targeted" as used herein refer to retroviral vector particles or virus-like particles thereof that induce preferential transduction or virus-like-particle uptake in target cells. Thus, the transduction of pseudotyped retrovirus vector particles or induced uptake of pseudotyped virus-like particles thereof is 10-fold higher, preferentially 100-fold higher, most preferentially 1000-fold higher on said target cells than on non-target cells. In the present invention this is achieved by incubating cells with a tagged polypeptide in the presence of a pseudotyped retroviral vectors or virus-like particles thereof that comprises an envelope protein with antigen binding activity with reduced or ablated interaction with its native receptor(s) and a fusion polypeptide comprising an antigen binding domain specific for a tag of a tagged polypeptide at the ectodoman of said envelope protein. For Paramyxoviridae H/HN and G proteins are proteins with antigen binding activity.

Thus, the tropism of a selective or targeted retroviral vector particle or virus-like particle thereof of the present invention is not defined by the tropism of the virus the H protein is derived from, but, depending on the specificity of the tagged polypeptide for a cell surface antigen of a target cell. As used herein, the polypeptide with an antigen binding domain specific for tag of tagged polypeptide fused the envelope protein with antigen binding activity has reduced or ablated interaction with any antigen expressed on the cell surface. For selective retroviral vectors or virus-like particles thereof pseudotyped with measles virus envelope proteins, the truncated protein H fused to the polypeptide comprising an antigen binding domain specific for a tag of a tagged polypeptide as disclosed herein must have mutations that generally reduce or ablate productive interactions with its native receptors. Such mutations are well-known in the art. A mutation that ablates interaction of measles H protein with CD46 is e.g. the point mutation at position Y481, F431, V451, Y452, A527, P486, 1487, A428, L464, G546, S548, F549 wherein these amino acids are replaced with another amino acid and this mutation prevents or assists in preventing interaction of the H protein with CD46. Alternatively, replacement of all five consecutive residues 473 to 477 in H protein with alanine may prevent interaction of H protein with CD46. Any of the above cited mutations maybe combined with each other For example, the following introduction of mutations ablates productive interaction of the measles H protein with CD46 and SLAM, respectively: Y481A R533A. (Nakamura et al. (2004), Nakamura et al. (2005), Vongpunsawad et al. (2004), Masse et al. (2002), Masse et al. (2004), Patterson et al. (1999)). In another embodiment, the Hmut protein also includes the mutations S548L and F549S, which lead to a more complete ablation of residual infectivity via CD46. Also, the mutation of the residues V451 and Y529 ablates productive interaction with CD46 and SLAM. Alternative mutations for ablating/preventing interaction of the H protein with CD46 have been described above. All of these mutations, which are introduced into the truncated H proteins in order to reduce or ablate the natural receptor usage, are located in the ectodomain of the measles H protein. For preventing interaction of the H protein with SLAM one of the following residues may be replaced with any other amino acid, in particular, alanine: 1194, D530, Y553, T531, P554, F552, D505, D507.

For nectin-4, mutations have been proposed in the art which abolish binding to this receptor as well. For example, Tahara et al. show that amino acid substitutions F483A, Y541S and Y543S of wt measles virus H protein result in an ablated fusion activity on Nectin-4 positive cells (Tahara et al. (2008)). This has been confirmed by Liu et al. showing that amino acid substitutions F543A and P497S of the Edmonston strain H abolish infection by vesicular stomatitis virus pseudotyped with Edmonston strain F and H envelope proteins (Liu et al. (2014)). There are further residues on the surface of the H molecule which are well conserved among different morbilliviruses that may be involved in Nectin-4 dependent fusion, e.g. Phe483, Asp521, Leu522, Tyr524, Tyr541, Tyr543, Ser544, Arg547, Ser550, and Tyr551 (Tahara et al. (2008)). This suggests that further mutations might be helpful for preventing interaction with Nectin-4. Lentiviral or gammaretroviral vector particles or virus-like particles thereof pseudotyped with truncated F proteins and mutated H proteins additionally displaying at their ectodomain a polypeptide comprising an antigen binding domain specific for a tag of a tagged polypeptide, wherein said tagged polypeptide is specific for a cell surface marker of a target cell, no longer enter cells via CD46, SLAM and/or nectin-4, but are rather targeted to and enter only those cells displaying the respective corresponding markers at their surface via the anti-tag domain of the polypeptide comprising an antigen binding domain specific for a tag fused to the truncated protein H and the tagged polypeptide.

For selective retroviral vectors or virus-like particle thereof pseudotyped with Nipah envelope proteins reduced or ablated interactions of the G protein to the native receptors ephrin-B2 and ephrin-B3 is required. Residues within the G protein were identified by screening mutants resulting in variants with ablated receptor binding ability (Bender et al. (2016)). E501, W504, Q530, E533 were either single mutated or in combination. The combined mutation of E501A, W504A, Q530A, E533A showed completely ablated receptor binding ability for both receptors ephrin-B2 and ephrin-B3.

A pseudotyped retroviral vector particle or virus-like particle thereof "derived from", for example, HIV-1, as used in the present invention, refers to a particle in which the genetic information for the RNA and/or the Gag and Pol proteins comprised by the vector particle originally stems from said retrovirus, in the above case, HIV-1. The original retroviral genome can comprise mutations, such as deletions, frame shift mutations and insertions.

The term "cytoplasmic portion", "cytoplasmic tail" or "cytoplasmic region", as used in herein refers to the portion of the respective protein that is adjacent to the transmembrane domain of the protein and, if the protein is inserted into the membrane under physiological conditions, extends into the cytoplasm. Within Paramyxoviridae all envelope proteins with antigen-binding function are characterized to date as type II membrane proteins, meaning that the cytoplasmic domain is located at the N-terminus of the envelope protein.

For the measles F protein, the transmembrane domain is identified by five amino acid sequence (SEQ ID NO: 3), for the measles H protein, the domain is identified by four amino acid sequence (SEQ ID NO: 4). The cytoplasmic portion of the measles F protein usually consists of the 33 C-terminal amino acids, the sequence for measles Edmonston strain can be found in SEQ ID NO: 5. The cytoplasmic portion of the measles H protein typically consists of 34 N-terminal amino acids, the sequence for measles Edmonston strain can be found in SEQ ID NO: 6.

For the Nipah G protein, the transmembrane domain is usually identified by the amino acid sequence as shown in SEQ ID NO: 7 and cytoplasmic portion as shown in SEQ ID NO: 8.

For the Nipah F protein, the transmembrane domain is usually defined by the amino acid sequence as shown in SEQ ID NO: 9 and the cytoplasmic portion usually consists of the amino acid sequence as shown in SEQ ID NO: 10.

The term "truncated", as used in the present invention, refers to a deletion of amino acid residues of the designated protein. It is clear to the skilled person that a protein is encoded by a nucleic acid. Thus, "truncated" also refers to the corresponding coding nucleic acids in a nucleic acid molecule that codes for a given "truncated" protein.

Furthermore, it is to be understood that the nucleic acid molecules encoding for a specific truncated or modified protein are likewise encompassed, and vice versa In the present invention, specific reference is made to "truncated H", "truncated G" or "truncated F" proteins, which designates the Paramyxoviridae, preferably measles H protein, Nipah G protein and Nipah or measles F proteins, respectively, whose cytoplasmic portion has been partly or completely truncated, i.e. amino acid residues (or coding nucleic acids of the corresponding nucleic acid molecule encoding the protein) have been deleted.

The cytoplasmic portion of the F protein is located at the C-terminus of the protein.

For all envelope protein with the cytoplasmic portion located at the C-terminus one begins counting from the C-terminal end of the protein when ascertaining the desired sequence. As an example, for the F protein derived from measles Edmonston strain FcΔ30 would refer to an F protein having a cytoplasmic portion with the amino acid sequence "RGR".

By contrast, the cytoplasmic portion of the H, HN or G protein is located at the N-terminus. Thus, one begins counting at the second amino acid residue of the N-terminal end of the H, HN or G protein (i.e. omitting the first methinonine residue) when ascertaining the desired sequence. It is disclosed in WO2008037458A2 that the cytoplasmic domain of the measles F protein can be truncated to comprise at least 1 positively charged amino acid residue and the cytoplasmic portion of the H protein can be truncated to comprise at least 9 consecutive amino acid residues of the C-terminal cytoplasmic portion of the H protein plus an additional methionine at the N-terminus. However, a further truncation of the cytoplasmic portion of the H protein is expected to be feasible, if the H protein is truncated to allow efficient pseudotyping and still has fusion support function.

Modifications that allow truncation for efficient pseudotyping may be combined with modifications that ablate native receptor binding function.

The person skilled in the art will readily be able to introduce mutations as, for example, additions and deletions, into a given nucleic acid or amino acid sequence.

The proteins of the present invention further includes functional homologs. A protein is considered a functional homolog of another protein for a particular function, if the homolog has a similar function as the original protein. The homolog can be, for example, a fragment of the protein, or a substitution, addition, or deletion mutant of the protein.

Determining whether two amino acid sequences are substantially homologous is typically based on FASTA searches. For example, the amino acid sequence of a first protein is considered to be homologous to that of a second protein if the amino acid sequence of the first protein shares at least about 70% amino acid sequence identity, preferably at least about 80% identity, and more preferably at least about 85%, 90%, 95% or 99% identity, with the sequence of the second protein.

The terms "Psi positive" and "psi negative", as used in the present application, refer to a nucleic acid molecule where the retroviral psi element is present and absent, respectively. The psi element is a cis-acting signal located near the 5' end of the retroviral genome and designates a packaging signal, which is of importance during assembly of the viruses and leads to the incorporation of the viral RNA into the viral core. Thus, a psi negative RNA does not comprise the retroviral psi element and consequently will not be assembled into a vector particle of the present invention; in contrast, a psi positive RNA that does comprise said psi element will be effectively assembled into the vector particle.

The terms "Titer" or "transduction efficiency" is used as a means to characterize and compare vector particles with regard to their ability to transduce their target cells. Thus, vector particles having an "increased titer" or an "increased transduction efficiency" are able to transduce a higher number of cells at a given vector particle volume than other vector particles with the same volume.

The term "antigen expressed on the surface of a (target) cell" or "cell (surface) marker", as used in the present invention, refers to a molecule present on the surface of a cell, preferentially on a target cell. Such molecules can be, inter alia, peptides or proteins that may comprise sugar chains or lipids, clusters of differentiation (CDs), antibodies or receptors. Since not all populations of cells express the same cell markers, a cell marker can thus be used to identify, select or isolate a given population of cells expressing a specific cell marker. As an example, CD4 is a cell marker expressed by T helper cells, regulatory T cells, and dendritic cells. Thus, T helper cells, regulatory T cells, and dendritic cells can be identified, selected or otherwise isolated, inter alia by a FACS cell sorter, by means of the CD4 cell marker.

The term "tagged polypeptide" as used herein refers to a polypeptide that has bound thereto directly or indirectly at least one additional component, i.e. the tag. The tagged polypeptide as used herein is able to bind an antigen expressed on a target cell. The polypeptide may be an antibody or antigen binding fragment thereof that binds to an antigen expressed on the surface of a target cell such as a tumor associated antigen on a cancer cell. The polypeptide of the tagged polypeptide alternatively may a cytokine or a growth factor or another soluble polypeptide that is capable of binding to an antigen of a target cell.

The term "adapter" or "adapter molecule" as used herein refers to a tagged polypeptide that can bind to an antigen of a target cell, e.g. antibody or antigen binding fragment thereof, and has bound thereto directly or indirectly at least one additional component, i.e. the tag. The adapter or adapter molecule may by a tagged antibody or antigen binding fragment thereof, a cytokine or a growth factor or another soluble polypeptide that is capable of binding to an antigen of a target cell.

The tag may be e.g. a hapten or dextran and the hapten or dextran may be bound by the antigen binding domain of the polypeptide comprising an antigen binding domain specific for the tag. Haptens such as e.g. FITC, biotin, PE, streptavidin or dextran are small molecules that elicit an immune response only when attached to a large carrier such as a protein; the carrier may be one that also does not elicit an immune response by itself. Once the body has generated antibodies to a hapten-carrier adduct, the small-molecule hapten may also be able to bind to the antibody, but it will usually not initiate an immune response; usually only the hapten-carrier adduct can do this.

The term "polypeptide comprising an antigen binding domain specific for a tag" as used herein refers to a polypeptide that can bind a tag of a tagged polypeptide. The tagged polypeptide is different from the polypeptide that comprises the antigen binding domain specific for the tag. The polypeptide comprising the antigen binding domain specific for a tag may be an antibody or antigen binding fragment thereof that binds to said tag of the tagged polypeptide.

Alternatively, the "tagged polypeptide" may be a "target cell binding molecule" (TCBM) that is bound by the antigen binding domain of the fused polypeptide comprising the antigen binding domain specific for a tag, wherein said antigen binding domain now is an anti-linker/label epitope (LLE) binding domain, i.e. a specific variant of a tag binding domain. The adaptable system of retroviral vector particle or virus-like particle thereof that uses TCBM and the (vector) particle as disclosed herein is briefly described in the following.

The lentiviral or gammaretroviral vector particle or virus-like particle thereof as disclosed herein may comprise a polypeptide comprising an antigen binding domain specific for a LLE of a TCBM fused to the truncated protein having receptor binding activity, e.g. protein H, wherein said antigen binding domain specific for a LLE is capable of discriminating between a naturally occurring molecule in a subject and a target cell binding molecule (TCBM) comprising an antigen binding molecule (ABM), a label moiety (LaM) and a linker moiety (LiM), wherein said LiM conjugates said ABM and said LaM. The ABM may be the polypeptide part of said tagged polypeptide. The label moiety (LaM) may be a naturally occurring molecule in a subject or a derivative thereof. The linker moiety (LiM) may be coupled to the label moiety (LaM). The LiM and LaM represent together the tag part of said tagged polypeptide.

The retroviral vector particle or virus-like particle thereof with the LLE binding domain binds TCBMs with LaM and a certain LiM with higher affinity than the endogenous label moiety without linker moiety. Thereby having an improved recognition/binding of TCBMs under physiological conditions where the endogenous LaM might be present.

The benefit of this approach is that the LaM that allows for an adaptable system of retroviral vector particle or virus-like particle thereof is non-immunogenic as it is a naturally occurring molecule endogenous to the subject. The LaM is a self-antigen, the LaM coupled to the LiM is a modified self-antigen, which build a novel epitope, the linker/label epitope (LLE), and the LLE is better bound by the LLE binding domain of the polypeptide comprising the antigen binding domain specific for the LLE than the natural occurring molecule in the subject.

The naturally occurring molecule may be a molecule present in the circulatory system of a subject, but is bound at a lower affinity than the TCBM by the retroviral vector system as as disclosed herein. Preferentially, the naturally occurring molecule in a subject may be an extracellular molecule or a molecule with partial extracellular structure, more preferentially, the naturally occurring molecule in a subject may be a human non-nuclear protein.

The linker moiety and label moiety are part of the target cell binding molecule (TCBM) that also comprises an antigen binding moiety (ABM), wherein the linker moiety conjugates the LaM and the ABM. Generally, said ABM is directed against an antigen expressed on the surface of a target cell.

By administration of TCBM along with the adaptable retroviral vector particle or virus-like particle thereof as disclosed herein target to only those cells expressing the antigen (marker) on the surface of the target cells, thereby selectively transducing the target cells. The adaptable system of retroviral vector particle or virus-like particle thereof as disclosed herein can be used as "universal" retroviral vector particle or virus-like particle thereof system to target a wide variety of target cells, e.g. a wide variety of tumors without the need to prepare separate constructs of retroviral vector particle or virus-like particle thereof. The label/linker epitope (LLE) of the TCBM recognized by the LLE binding domain of the polypeptide comprising said LLE binding domain may also remain constant. It is only the ABM of the TCBM that needs to be altered to allow the system to target target cells of different identity.

The anti-LLE binding domain of said polypeptide utilizes TCBMs as the bridge between the retroviral vector particle or virus-like particle thereof and the target cells expressing the antigen. The TCBM comprises a label moiety (LaM) on one end of the molecule and an antigen binding moiety (ABM) on the other end, connected by a linker moiety. The sole requirement for the identity of the label moiety is only in that it must be a naturally occurring molecule in a subject (a self-antigen) and that the linker moiety conjugated variant thereof can be recognized and bound by a LLE binding domain of said polypeptide with higher affinity to the linker moiety conjugated variant thereof (the modified self-antigen) than to the non-linker moiety conjugated, naturally occurring variant.

Every molecule that might be capable of generating a LLE may be used as a linker moiety. The sole requirement for the identity of a linker moiety is that the linker moiety may be chemically conjugated (or coupled) to a label moiety or genetically (recombinantly) encoded and should be able to generate a new epitope at the context, the interface and/or environment of linker moiety and label moiety. The LiM may be preferentially a molecule that does not evoke or does not tend to evoke an immune reaction in the subject, e.g. the LiM is a self-antigen. In this case the interface of the LaM and LiM generates a novel epitope, the LLE.

The LiM may be e.g selected from the group consisting of peptides, proteins, nucleic acids, carbohydrates, polyhydroxyalkanoates, alkyl chains, alkanoic acids, carboxylic acids (e.g. ε-aminocaproic acid (6-aminohexanoic acid) or 6-(6-aminohexanamido)hexanoic acid) farnesyls, polyethylene glycols, lipids and derivatives thereof.

An especially preferred LiM may be a 6-(6-aminohexanamido) hexanoyl moiety, e.g. derived from 6-(6-aminohexanamido)hexanoic acid or 6-(6-aminohexanamido) hexanoic active ester, or a 6-aminohexanoyl moiety, e.g. derived from 6-aminohexanoic acid or 6-aminohexanoic active ester. The adaptable retroviral vector particle or virus-like particle thereof system may be a system having a polypeptide comprising an LLE binding domain, wherein said LaM is biotin and said LiM is a 6-(6-aminohexanamido) hexanoyl linker moiety or a 6-aminohexanoyl linker moiety.

The term "antibody" as used herein is used in the broadest sense to cover the various forms of antibody structures including but not being limited to monoclonal and polyclonal antibodies (including full length antibodies), multispecific antibodies (e.g. bispecific antibodies), antibody fragments, i.e. antigen binding fragments of an antibody, immunoadhesins and antibody-immunoadhesin chimeras, that specifically recognize (i.e. bind) an antigen. "Antigen binding fragments" comprise a portion of a full-length antibody, preferably the variable domain thereof, or at least the antigen binding site thereof ("an antigen binding fragment of an antibody"). Examples of antigen binding fragments include Fab (fragment antigen binding), scFv (single chain fragment variable), single domain antibodies, diabodies, dsFv, Fab', diabodies, single-chain antibody molecules, and multispecific antibodies formed from antibody fragments. As used herein, the term "antigen" is intended to include substances that bind to or evoke the production of one or more antibodies and may comprise, but is not limited to, proteins, peptides, polypeptides, oligopeptides, lipids, carbohydrates such as dextran, haptens and combinations thereof, for example a glycosylated protein or a glycolipid. The term "antigen" as used herein refers to a molecular entity that may be expressed on the surface of a target cell and that can be recognized by means of the adaptive immune system including but not restricted to antibodies or TCRs, or engineered molecules including but not restricted to endogenous or transgenic TCRs, CARs, scFvs or multimers thereof, Fab-fragments or multimers thereof, antibodies or multimers thereof, single chain antibodies or multimers thereof, or any other molecule that can execute binding to a structure with high affinity.

The term "expression" as used herein is defined as the transcription and/or translation of a particular nucleotide sequence driven by its promoter in a cell.

The term "epitope" means the part of an antigen that may be recognized by the immune system, specifically by antibodies, B cells, or T cells. For example, the epitope is the specific piece of the antigen to which an antibody or antigen binding fragment thereof binds.

The terms "linker/label epitope" (LLE) or "label/linker epitope" as used herein can be used interchangeably and refer to an epitope formed by the context, the interface and/or environment of conjugated linker moiety and label moiety of the TCBM as disclosed herein.

The epitope generated by the coupling of the label moiety with a linker moiety does not occur naturally in a subject. The generated epitope comprises a part of said LaM and a part of said LiM. Preferentially, the LLE does not evoke or does not tend to evoke an immune reaction in a subject intended to be treated with the adaptable system as disclosed herein. The only requirement for the LLE is that it is an epitope for the polypeptide comprising the LLE binding domain. An LLE binding domain of said polypeptide as disclosed herein that is derived from an epitope recognizing molecule such as an antibody that recognizes the label/linker epitope binds with a higher preference to the newly created epitope, i.e. the label/linker epitope (the modified self-antigen), than to the endogenous label moiety without linker moiety, i.e. the naturally occurring molecule in the subject (the self-antigen).

Said LLE binding domain binds with an at least twofold, preferentially at least 5-fold, more preferentially at least 10-fold higher affinity to said LLE than to the said naturally occurring molecule.

The "circulatory system" is an organ system of a subject that permits blood to circulate and transport nutrients (such as amino acids and electrolytes), oxygen, carbon dioxide, hormones, and blood cells to and from the cells in the body to provide nourishment and help in fighting diseases, stabilize temperature and pH, and maintain homeostasis. The circulatory system comprises two separate systems: the cardiovascular system, which distributes blood, and the lymphatic system, which circulates lymph.

The term "naturally occurring molecule in a subject or a derivate thereof" as used herein refers to molecules or substances in a subject, preferentially said molecules are located extracellularly or have at least an extracellular part, e.g. a transmembrane spanning protein. The naturally occurring molecule may exist in free form or covalently or non-covalently bound to another molecule, e.g. bound to a protein. For example, biotin exists in free form circulating in the blood system, but also bound to e.g. plasmaprotein.

Due to this requirement these molecules are non-immunogenic as they are endogenous molecules (self-antigens) of the subject. As an example, biotin is a naturally occurring molecule in a subject as it is a circulatory molecule in the blood system (circulatory system) of a subject. The term "derivative thereof" means in this context that said naturally occurring molecule in a subject may undergo some minor modifications without changing the nature of said molecule. Said modifications are not identical with the conjugation of the linker moiety to said molecule. The term "tumor" is known medically as a neoplasm. Not all tumors are cancerous; benign tumors do not invade neighboring tissues and do not spread throughout the body.

The term "cancer" is known medically as a malignant neoplasm. Cancer is a broad group of diseases involving unregulated cell growth and includes all kinds of leukemia. In cancer, cells (cancerous cells) divide and grow uncontrollably, forming malignant tumors, and invading nearby parts of the body. The cancer may also spread to more distant parts of the body through the lymphatic system or bloodstream. There are over 200 different known cancers that affect humans.

EXAMPLES

Example 1: Principle of the Adaptable Retroviral Vector System

Figure 1:
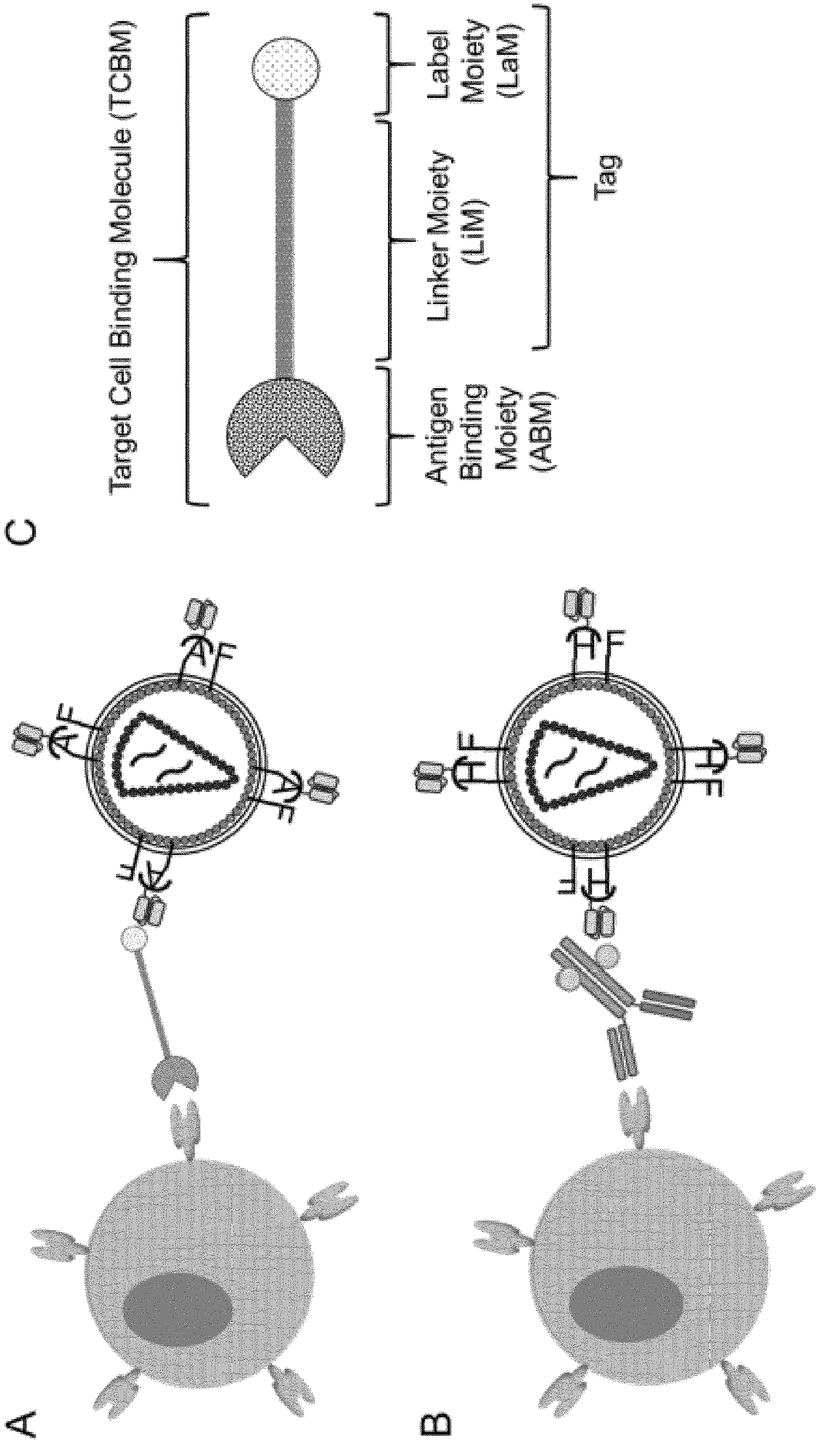
FIG. 1: Schematic representation of adapter mediated transduction

Envelope proteins with antigen binding activity with reduced or ablated interaction with their native receptors were equipped with scFvs specific for biotin (SEQ ID NO: 1 and 2), clone Bio3-18E) and dextran (SEQ ID NO: 13 and 14), respectively. For the biotin specific scFv, the LLE principle (FIG. 1C) as disclosed herein may be applied, i.e. the antigen binding domain of the scFV Bio3-18E binds with higher preference to biotin (LaM) that is coupled to the 6-(6-aminohexanamido) hexanoyl moiety or a 6-aminohexanoyl moiety (LiM) than to free biotin or biotin coupled with other linkers. LiM connects biotin and the antigen binding moiety (ABM) of the target binding molecule (TCBM).

Two chains of the scFVs are linked via a 3(G4S) linker (SEQ ID NO: 11) and may be present in either orientations (VH-VL or VL-$V_H$). The orientation can influence expression levels, stability, affinity to the tag of the tagged polypeptide ant the titer of the pseudotyped retroviral vector or virus-like particle thereof, respectively. A His tag (SEQ ID NO: 12) has been added to the C-terminal end of the protein with antigen binding activity protein, to enable measuring surface expression by flow cytometry (FIG. 2).

DNA encoding the scFV of the dextran specific (SEQ ID NO 13 and 14) and biotin specific antibody (SEQ ID NO: 1 and 2) in VH-VL orientation were obtained by gene synthesis (ATUM, Newark, California). Flanking restrictions sites SfiI and NotI were inserted to enable insertion into the SfiI and NotI digested Hmut encoding plasmid pCG-Hmut (Anliker et al. (2010)). DNA encoding the biotin-specific scFV in VL-VH orientation was obtained by PCR using a plasmid encoding for the scFV in VL-VH orientation with primers adding the restriction sites. The amplified scFV was inserted via SfiI and NotI into the digested Hmut encoding plasmid as described before. Cell surface expression of the recombinant proteins with antigen binding activity is crucial in terms of productivity of the pseudotyped retroviral vector or virus-like particle thereof. Surface expression was determined by transient transfection of HEK-293T cells that were seeded in 6 wells with a density of 8×105 cells/well the day before transfection. Of each construct 1.5 sg DNA was transfected. Two days post transfection one part of the cells was stained with His tag specific antibodies according the instructions of the manufacturer (Miltenyi Biotec, Cat. No. 130-092-691), followed by flow cytometry to determine the ratio of His positive cells (FIG. 3A). Another part of the cells was stained with an antibody specific for CD25 conjugated to biotin and a fluorescent protein (Miltenyi Biotec, Cat. No. 130-019-010). HEK-293T cells are CD25 negative, meaning only protein with antigen binding activity containing the Bio3-18E scFV is detected. Thereby, quantification of labeled cells can be indirectly correlated to the antigen binding capacity of the envelope protein (FIG. 3B).

Example 2: Generation of a Tag Specific, Pseudotyped Retroviral Vector

Pseudotyped retrovrial vector particles specific for a tag of tagged polypeptide were generated by transient transfection of HEK-293T cells. HEK-293T cells that were seeded in T175 flasks in DMEM/10% FCS (Biowest, Cat. No. 12362; Biochrom, Cat. No. SO415) the day before were transfected with a plasmid encoding for the H protein, a plasmid encoding for the F protein, a packaging plasmid encoding gag/pol/rev and a psi-positive transfer vector plasmid encoding GFP. The pseudotyped retroviral vector particles were harvested 48 h post transfection. To remove cellular debris, the supernatant was collected, centrifuged for 10 min at 1000 rpm, followed by filtration through a 0.45 μm filter. To concentrate, the filtered supernatant was centrifuged through a 20% sucrose (Sigma Aldrich, Cat. No. 84097-250 g, 20% w/v in PBS) cushion for 24 h at 4° C. with 5350×g. The pelleted retroviral vectors were resuspended in 250 μl precooled PBS, aliquoted and stored at −80° C. for later use.

Example 3: Generation of Tagged Polypeptides

Random labeling of proteins like antibodies or fragments thereof with LC-LC-biotin was performed according to protocols well known in the art. Antibodies or fragments thereof were rebuffered into 1×PBS/2 mM EDTA/0.5% BSA by running over equilibrated Amicon Ultra-filter units according to the manufacturer instructions. Biotin-LC-LC-NHS was added to the rebuffered protein followed by incubation at room temperature (21° C.) for 1 h. Remaining biotin-LC-LC-NHS was removed by gel filtration. The protein content of the collected fractions was determined. Biotinylation was confirmed by incubation of the tagged antibody or fragment thereof on a cell line expressing the antigen of said antibody or fragment thereof. Bound tagged antibody was detected with a fluorochrome conjugated anti-biotin antibody (Miltenyi Biotec, Cat. No. 130-104-563) and flow cytometry.

Example 4: Titration of a Tag Specific, Pseudotyped Retroviral Vector

Pseudotyped retroviral vector particles were titrated on HT1080 cells in the absence of the tagged polypeptide. Therefore, proteins on the cell surface were randomly labeled with LC-LC-biotin using by Biotin-LC-LC-NHS. HT1080 resuspended in 1 ml PBS were supplemented with Biotin-LC-LC-NHS followed by an incubation at 4° C. at constant mixing. After removing cell-free supernatant, cells were washed and seeded with 1×105 cells/well in 24-wells in cultivation media (DMEM, 10% FCS) until the cells were completely adherent. Successful biotinylation was confirmed by staining with a fluorochrome conjugated anti-biotin antibody (Miltenyi Biotec, Cat. No. 130-090-856) and flow cytometry (FIG. 4A). The GFP encoding vector particles were serially diluted in a DMEM containing Polybrene® (Sigma Aldrich, Cat. No. H9268-5G). 72 h post transduction the transduction efficiency was determined by flow cytometry determining the ratio of GFP positive (FIG. 4A). The ratio of GFP positive cells, the dilution factor and the volume of retroviral applied is used to calculate the retroviral vector titer (i.e. transducing units per volume (TU/ml) (FIG. 4B).

Example 5: Transduction of Cell Lines with Retroviral Vector

The transduction of unbiotinylated HT1080 cells is performed as described (Example 4). Raji cells were transduced at 3.3×105 cells/ml in 48 well plates in RPMI, 2 mM stable glutamine (Biowest, Cat. No. L0501-500; Lonza, Cat. No. 882027-12) (FIG. 5-11). Retroviral vector was added to the cells, which were cultivated for at least 72 h until flow cytometry was performed to determine the ratio of transduced cells and the calculated titer. SupT1 were transduced at $1\times10^6$ cells/ml in RPMI, 2 mM stable glutamine seeded in 96 well U-bottom plates (FIG. 7, 8, 11). Retroviral vector was added to the cells, which were cultivated for at least 72 h until flow cytometry was performed to determine the ratio of transduced cells and the calculated titer. Jurkat cells were transduced in 48 well plates at a cell density of $2\times10^6$ cells/ml in RPMI, 2 mM stable glutamine (FIG. 5, 7, 9, 10). Retroviral vector was added to the cells, which were cultivated for at least 72 h until flow cytometry was performed to determine the ratio of transduced cells and the calculated titer. To verify the expression of the antigen expressed by target cell, staining with the tagged polypeptide followed by a fluorescently labelled α-biotin antibody (Miltenyi Biotec, Cat. No. 130-090-856) and flow cytometric analysis was performed.

Example 6: Selective Transduction with Adaptable Retroviral Vector System

To selectively transduce target cells with tag-specific retroviral vectors and tagged polypeptides specific for selected antigens, target cells were seeded in serum-free medium as described before (Example 5). Tagged antibodies or tagged Fab fragments were added to the cells in a concentration of 100 ng/ml to 1000 ng/ml (FIG. 7, 11,12). The cells were incubated with tagged polypeptide for at least 30 min at 4° C. Afterwards GFP encoding retroviral vector was added. Selectivity in mixed cell populations was shown with equal amounts of Raji and SupTI cells at a total density of $1\times10^6$ cells/ml in 48 well plates. The Raji specific transduction protocol was applied (FIG. 8).

Example 7: Optimization of the Adaptable Retroviral Vector System

The performance and applicability of the adaptable retroviral vector system was easily improved by determining the best order of combining cells, tag specific retroviral vector and tagged polypeptide altogether. Therefore, two components were preincubated followed by the addition of the third component. This assay was performed with α-CD20-Ab-tag as polypeptide, tag specific retroviral vector encoding GFP and Raji (CD20+) as target cells or Jurkat cells (CD20-) as non-target cells. First, α-CD20-Ab-tag and retroviral vector was combined in 300 μl RPMI for Raji cells or 150 μl for Jurkat cells using 1 μg/ml α-CD20-Ab-tag and a retroviral vector dose of MOI 0.05. After incubation at 4° C. for 30 min, target cells, either Raji or Jurkat, were resuspended in the preincubated retroviral vector/tagged polypeptide mix. Flow cytometry was performed at least 72 h post transduction (FIG. 5A).

Second, target or non-target cells were preincubated with retroviral vector, the cells were seeded in RPMI medium (150 μl for Jurkat, 300 μl for Raji). Viral vector was added to the cells with a MOI of 0.05, followed by incubation at 37° C. for 30 min. Afterwards the adapter molecule was added in a final concentration of 1 μg/ml. Flow cytometry was performed at least 72 h post transduction (FIG. 5B). For initial binding of the adapter to the cells, the target cells were seeded in 150 μl for Jurkat or 300 μl for Raji cells in RPMI and the adapter molecule was added at a final concentration of 1 μg/ml. After incubation for 30 min at 4° C., GFP encoding viral vector was added. Flow cytometry was performed at least 72 h post transduction (FIG. 5C). For all three protocol conditions RPMI supplemented with 10% FCS was added after 4 h of preincubation to a final volume of 1 ml.

In order to increase the transduction efficiency, Vectofusin-1® (Miltenyi Biotec, Cat. No. 130-111-163) was used (FIG. 6C). Vectofusin-1® was prepared in RPMI directly prior to the transduction. The volume of retroviral vector was mixed 1:2 with the corresponding volume of Vectofusin-1® for 5 min prior to the transduction. The mix was then added to the cells: 50 μl for Jurkat or 100 μl for Raji cells. As control, Polybrene® (Sigma Aldrich, Cat. No. H9268-5G) was applied (FIG. 6B).

The optimal concentration of the adapter molecule was exemplary determined for CD4 and CD20 specific tagged polypeptides on Jurkat cells (FIG. 10A) or Raji cells (FIG. 10B). Therefore, the protocol with initial binding of the adapter molecules with the cells was used.

To show selectivity under conditions prone to induce unspecific transduction, cells were transduced in the presence of serum, in the presence of untagged polypeptides and with a high retroviral vector dose (FIG. 9).

Example 8: Screening Method

In this example the pseudotyped retroviral vector particle or virus-like particle thereof is used to determine the specificity of unknown tagged polypeptide by incubating the unknown tagged polypeptide with either defined cells or mix of cells. The pseudotyped retroviral vector particle or virus-like particle thereof encodes a marker that allows to determine the cell type to which the unknown tagged polypeptide is bound. This approach can be carried out in vitro or in vivo using for instance, but not restricted to, mouse models.

Example 9: Adapter-LV Using Nipah Envelope Proteins for Pseudotyping

Adapter-LV pseudotyped with Nipah envelope proteins was generated by modifying the protocol as described before (Example 2) by using plasmids encoding for the G and F proteins of Nipah instead of the measles virus protein H, F encoding plasmids. Pseudotyped retroviral vector particles were titrated on Raji cells in the presence of α-CD20-Ab-tag as polypeptide. The Raji specific transduction protocol was applied as described before. GFP encoding retroviral vector particles were serially diluted in RPMI.72 h post transduction the transduction efficiency was determined by flow cytometry determining the ratio of EGFP positive cells. The measured ratio of GFP positive cells, the dilution factor and the volume of retroviral applied was used to calculate the retroviral vector titer (i.e. transducing units per volume (TU/ml). CD19 positive, CD20 positive Raji cells seeded in serum-free medium were selectively transduced with tag-specific, Nipah envelope protein pseudotyped retroviral vectors as described before (Example 5). Tagged adapter was added to the cells at a concentration of 100 ng/ml for at least 30 min at 4° C. GFP encoding Nipah envelope protein pseudotyped retroviral vectors were subsequently added. The transduction efficiency was determined 3 days post transduction by flow cytometric analysis. (FIG. 13).

Example 10: Targeted Protein Delivery Using Adapter-VLP

Pseudotyped retroviral VLPs were produced by modifying the production protocol for retroviral vectors (Example 2). HEK cells were transfected with the plasmids encoding the tag-specific measles H, plasmids encoding the measles F protein, plasmids encoding gag/pol/rev and gag/pol/rev/transgene encoding plasmids that contain a transgene of choice inserted between matrix and the capsid protein. As transgene eGFP or monomeric red fluorescent protein was used. The fluorescent proteins are released into the matured particles by adding flanking HIV-1 protease cleavage sites (Uhlig et al. (2015)). VLPs were titrated as described before (Example 4). Contrary to this, analysis was performed already 4 h post addition of the VLPs. To selectively transfer fluorescent proteins, tag-specific VLPs were added to CD4 positive, CD8 positive SupTI cells in serum-free medium in the absence (w/o) or presence of tagged or untagged adapter molecules specific for the antigen expressed by SupTI cells (Example 5). The adapter concentration was set to 100 ng/ml (10 ng/ml for α-CD8-AB). After incubation of the cells with adapter for at least 30 min at 4° C. VLPs were added at an MOI of 0.05. 4 hours later, the protein transfer rate was measured by flow cytometry FIG. 14A & 14B.

REFERENCES

Anliker, B., Abel, T., Kneissl, S., Hlavaty, J., Caputi, A., Brynza, J., Schneider, I. C., Munch, R. C., Petznek, H., Kontermann, R. E., et al. (2010). Specific gene transfer to neurons, endothelial cells and hematopoietic progenitors with lentiviral vectors. Nature methods 7, 929-935.

Bender, R. R., Muth, A., Schneider, I. C., Friedel, T., Hartmann, J., Pluckthun, A., Maisner, A., and Buchholz, C. J. (2016). Receptor-Targeted Nipah Virus Glycoproteins Improve Cell-Type Selective Gene Delivery and Reveal a Preference for Membrane-Proximal Cell Attachment. PLoS pathogens 12, e1005641.

Buchholz, C., Cattaneo, R., Cichutek, K., and Funke, S. (2009). Pseudotypisierung retroviraler vektoren, verfahren zur herstellung und verwendung davon fir gezielten gentransfer und screening mit hohem durchsatz, EP2066795 B9.

Chen, X., Zaro, J. L., and Shen, W. C. (2013). Fusion protein linkers: property, design and functionality. Advanced drug delivery reviews 65, 1357-1369.

Edes, I. (2016). Targeted transduction of T cell subsets for immunotherapy of cancer and infectious disease (Humboldt-Universitit zu Berlin, Lebenswissenschaftliche Fakultat).

Enkirch, T., Kneissl, S., Hoyler, B., Ungerechts, G., Stremmel, W., Buchholz, C. J., and Springfeld, C. (2013). Targeted lentiviral vectors pseudotyped with the Tupaia paramyxovirus glycoproteins. Gene therapy 20, 16-23.

Frecha, C., Costa, C., Negre, D., Gauthier, E., Russell, S. J., Cosset, F. L., and Verhoeyen, E. (2008). Stable transduction of quiescent T cells without induction of cycle progression by a novel lentiviral vector pseudotyped with measles virus glycoproteins. Blood 112, 4843-4852.

Friedel, T., Hanisch, L. J., Muth, A., Honegger, A., Abken, H., Pluckthun, A., Buchholz, C. J., and Schneider, I. C. (2015). Receptor-targeted lentiviral vectors are exceptionally sensitive toward the biophysical properties of the displayed single-chain Fv. Protein engineering, design & selection: PEDS 28, 93-106.

Hoop, M. (2014). Modulation of the transduction of pseudotyped lentiviral vectors and their application for the production of recombinant proteins, doi: 10.3929/ethz-b-000179875.

Kaikkonen, M. U., Lesch, H. P., Pikkarainen, J., Raty, J. K., Vuorio, T., Huhtala, T., Taavitsainen, M., Laitinen, T., Tuunanen, P., Grohn, O., et al. (2009). (Strept)avidin-displaying lentiviruses as versatile tools for targeting and dual imaging of gene delivery. Gene therapy 16, 894-904.

Khetawat, D., and Broder, C. C. (2010). A functional *henipavirus* envelope glycoprotein pseudotyped lentivirus assay system. Virology journal 7, 312.

Lee, B., Palomares, K., and Pernet, O. (2016). Nipah virus envelope pseudotyped lentiviruses and methods of their use, EP2844746 A1.

Liu, Y. P., Russell, S. P., Ayala-Breton, C., Russell, S. J., and Peng, K. W. (2014). Ablation of nectin4 binding compromises CD46 usage by a hybrid vesicular stomatitis virus/measles virus. Journal of virology 88, 2195-2204.

Masse, N., Ainouze, M., Neel, B., Wild, T. F., Buckland, R., and Langedijk, J. P. (2004).

Measles virus (MV) hemagglutinin: evidence that attachment sites for MV receptors SLAM and CD46 overlap on the globular head. Journal of virology 78, 9051-9063.

Masse, N., Barrett, T., Muller, C. P., Wild, T. F., and Buckland, R. (2002). Identification of a second major site for CD46 binding in the hemagglutinin protein from a laboratory strain of measles virus (MV): potential consequences for wild-type MV infection. Journal of virology 76, 13034-13038.

Metzner, C., Kochan, F., and Dangerfield, J. A. (2013). Postexit surface engineering of retroviral/lentiviral vectors. BioMed research international 2013, 253521.

Morizono, K., Xie, Y., Helguera, G., Daniels, T. R., Lane, T. F., Penichet, M. L., and Chen, I. S. (2009). A versatile targeting system with lentiviral vectors bearing the biotin-adaptor peptide. The journal of gene medicine 11, 655-663.

Nakamura, T., Peng, K. W., Harvey, M., Greiner, S., Lorimer, I. A., James, C. D., and Russell, S. J. (2005). Rescue and propagation of fully retargeted oncolytic measles viruses. Nature biotechnology 23, 209-214.

Nakamura, T., Peng, K. W., Vongpunsawad, S., Harvey, M., Mizuguchi, H., Hayakawa, T., Cattaneo, R., and Russell, S. J. (2004). Antibody-targeted cell fusion. Nature biotechnology 22, 331-336.

Palomares, K., Vigant, F., Van Handel, B., Pernet, O., Chikere, K., Hong, P., Sherman, S. P., Patterson, M., An, D. S., Lowry, W. E., et al. (2013). Nipah virus envelope-pseudotyped lentiviruses efficiently target ephrinB2-positive stem cell populations in vitro and bypass the liver sink when administered in vivo. Journal of virology 87, 2094-2108.

Patterson, J. B., Scheiflinger, F., Manchester, M., Yilma, T., and Oldstone, M. B. (1999). Structural and functional studies of the measles virus hemagglutinin: identification of a novel site required for CD46 interaction. Virology 256, 142-151.

Rasbach, A., Abel, T., Munch, R. C., Boller, K., Schneider-Schaulies, J., and Buchholz, C. J. (2013). The receptor attachment function of measles virus hemagglutinin can be replaced with an autonomous protein that binds Her2/neu while maintaining its fusion-helper function. Journal of virology 87, 6246-6256.

Roux, P., Jeanteur, P., and Piechaczyk, M. (1989). A versatile and potentially general approach to the targeting of specific cell types by retroviruses: application to the infection of human cells by means of major histocompatibility complex class I and class II antigens by mouse ecotropic murine leukemia virus-derived viruses. Proceedings of the National Academy of Sciences of the United States of America 86, 9079-9083.

Snitkovsky, S., and Young, J. A. (2002). Targeting retroviral vector infection to cells that express heregulin receptors using a TVA-heregulin bridge protein. Virology 292, 150-155. Tahara, M., Takeda, M., Shirogane, Y., Hashiguchi, T., Ohno, S., and Yanagi, Y. (2008).

Measles virus infects both polarized epithelial and immune cells by using distinctive receptor-binding sites on its hemagglutinin. Journal of virology 82, 4630-4637.

Uhlig, K. M., Schulke, S., Scheuplein, V. A., Malczyk, A. H., Reusch, J., Kugelmann, S., Muth, A., Koch, V., Hutzler, S., Bodmer, B. S., et al. (2015). Lentiviral Protein Transfer Vectors Are an Efficient Vaccine Platform and Induce a Strong Antigen-Specific Cytotoxic T Cell Response. Journal of virology 89, 9044-9060.

Vongpunsawad, S., Oezgun, N., Braun, W., and Cattaneo, R. (2004). Selectively receptor-blind measles viruses: Identification of residues necessary for SLAM- or CD46-induced fusion and their localization on a new hemagglutinin structural model. Journal of virology 78, 302-313.

The invention claimed is:

1. A combination of reagents configured for delivery of a gene or protein to a target cell, consisting of:

(i) a tagged polypeptide that comprises:

(a) an antigen binding moiety (ABM), which binds specifically to said antigen on the target cell;

(b) a label moiety (LaM), which is a hapten, and (c) a linker moiety (LiM), which conjugates the ABM to the LaM such that the LaM and LiM together form a linker/label epitope (LLE); and (ii) a pseudotyped Paramyxoviridae viral vector that contains said gene or protein for delivery to the target cell;

wherein the pseudotyped Paramyxoviridae viral vector is a lentiviral or gammaretroviral vector that comprises:

(a) a Paramyxoviridae attachment protein that has been genetically modified to remove constitutive cell binding activity, fused at or near the C-terminal of its ectodomain to a single chain antibody that comprises a binding domain that specifically binds to the LLE on the tagged polypeptide, and (b) a Paramyxoviridae fusion protein that has fusion activity;

wherein said attachment protein is a Morbillivirus hemagglutinin (H) or a *Henipavirus* glycoprotein (G); and wherein said fusion (F) protein is from the same Paramyxoviridae genus as the attachment protein;

wherein contacting the target cell with said viral vector in the presence of said tagged polypeptide results in delivery of said gene or protein into the target cell.

2. The combination of claim 1, wherein component (ii) is a pseudotyped retroviral vector particle configured for gene delivery to the target cell.

3. The combination of claim 1, wherein component (ii) is a virus-like particle configured for protein delivery to the target cell.

4. The reagent combination of claim 1, wherein said modified attachment protein is not human tropic.

5. The reagent combination of claim 1, wherein in the presence of the tagged polypeptide, delivery of the gene or protein to the target cell by the viral vector is at least 10-fold higher than to non-target cells.

6. The reagent combination of claim 1, wherein said modified attachment protein lacks at least a part of its cytoplasmic region.

7. The reagent combination of claim 1, wherein said fusion protein lacks at least part of its cytoplasmic region.

8. The reagent combination of claim 1, wherein said Morbillivirus is a measles virus.

9. The reagent combination of claim 1, wherein said tagged polypeptide is a tagged antibody or an antigen binding fragment thereof that binds to an antigen expressed on the surface of said target cell, and wherein the tag a hapten.

10. The reagent combination of claim 1, wherein said single chain antibody on the modified attachment protein binds with at least two-fold higher affinity to said LLE than to the LaM without the LiM.

11. The reagent combination of claim 1, wherein said LaM is biotin or a derivative thereof, and said LiM is a 6-(6-aminohexanamido) hexanoyl moiety or a 6-amino-hexanoyl moiety.

12. The reagent combination of claim 1, wherein said single chain antibody on the modified attachment protein comprises SEQ ID NO: 1 ($V_H$) and SEQ ID NO: 2 ($V_L$) in either order.

13. The reagent combination of claim 1, wherein the tagged polypeptide and the pseudotyped Paramyxoviridae viral vector are formulated together as part of a single pharmaceutical composition, which further comprises one or more physiologically acceptable carriers or excipients.

14. A method for delivering a gene or a protein to target cells ex vivo, comprising:

(a) providing the reagent combination of claim 1;

(b) preincubating the target cells with said tagged polypeptide; and then (c) contacting the target cells with said pseudotyped Paramyxoviridae viral vector, thereby inducing delivery of said gene or said protein into at least some of the target cells.

15. The reagent combination of claim 1, wherein said attachment protein is hemagglutinin (H) of Morbillivirus.

16. The reagent combination of claim 1, wherein said attachment protein is guanine nucleotide binding (G) protein of Henipavirus.

17. The reagent combination of claim 1, wherein the LaM is an antigen or epitope that occurs naturally in the circulation of humans.

18. The reagent combination of claim 1, wherein the LaM is biotin.

19. The reagent combination of claim 8, wherein said Morbillivirus is the Edmonston strain of measles virus.

20. A method of preparing a combination of reagents for delivery of a gene or protein to a target cell, the method comprising:

(1) selecting a target antigen on the target cell;

(2) constructing a tagged polypeptide that comprises a tag conjugated to an antigen binging moiety (ABM) that is specific for the selected target antigen;

(3) designing a Paramyxoviridae attachment protein that comprises a Morbillivirus hemagglutinin (H) or a Henipavirus glycoprotein (G) modified to remove constitutive activity for binding to the target cell, fused at or near the C-terminal of its ectodomain to a single chain antibody that specifically binds said tag;

(4) constructing a pseudotyped Paramyxoviridae viral vector that comprises said modified attachment protein and a fusion (F) protein from the same Paramyxoviridae genus as the attachment protein; and (5) packaging said gene or protein in the pseudotyped viral vector;

wherein said polypeptide and said pseudotyped viral vector constitute said combination of reagents;

wherein contacting the target cell with said viral vector in the presence of said tagged polypeptide results in delivery of said gene or protein into the target cell.

21. The method of claim 20, wherein the combination of reagents is configured for delivery of a gene into a target cell.

22. The method of claim 20, wherein the combination of reagents is configured for delivery of a protein into a target cell.

23. The method of claim 20, wherein the modified Paramyxoviridae attachment protein comprises a Morbillivirus hemagglutinin (H).

24. The reagent combination of claim 23, wherein said Morbillivirus is a measles virus.

25. The method of claim 24, wherein said Morbillivirus is the Edmonston strain of measles virus.

26. The method of claim 20, wherein the modified Paramyxoviridae attachment protein comprises a Henipavirus glycoprotein (G).

* * * * *